(12) United States Patent
Helbert et al.

(10) Patent No.: US 8,669,089 B2
(45) Date of Patent: Mar. 11, 2014

(54) ULVAN LYASE, METHOD FOR MANUFACTURING SAME, AND USES THEREOF

(75) Inventors: William Helbert, Saint Martin d-Uriage (FR); Pi Nyvall-Collen, Roscoff (FR); Yannick Lerat, Ploubazlanec (FR); Jean-François Sassi, Ploubazlanec (FR)

(73) Assignees: Centre National de la Recherche Scientifique-CNRS, Paris (FR); Centre d'Etude et de Valorisation des Algues-CEVA, Pleubian (FR); Universite Pierre et Marie Curie, Paris (FR)

( * ) Notice: Subject to any disclaimer, the term of this patent is extended or adjusted under 35 U.S.C. 154(b) by 0 days.

(21) Appl. No.: 13/704,911

(22) PCT Filed: Jun. 16, 2011

(86) PCT No.: PCT/FR2011/051384
§ 371 (c)(1),
(2), (4) Date: May 10, 2013

(87) PCT Pub. No.: WO2011/157966
PCT Pub. Date: Dec. 22, 2011

(65) Prior Publication Data
US 2013/0230889 A1     Sep. 5, 2013

(30) Foreign Application Priority Data

Jun. 18, 2010 (FR) ..................................... 10 02588

(51) Int. Cl.
| | | |
|---|---|---|
| *C12N 9/88* | (2006.01) | |
| *C12N 15/00* | (2006.01) | |
| *C12N 1/12* | (2006.01) | |
| *C07H 21/04* | (2006.01) | |

(52) U.S. Cl.
USPC ..................... 435/232; 435/257.1; 435/252.3; 435/320.1; 530/350; 536/23.2

(58) Field of Classification Search
USPC ................. 435/183, 252.3, 320.1, 6, 23, 622; 536/23.1, 23.2; 530/350
See application file for complete search history.

(56) References Cited

FOREIGN PATENT DOCUMENTS

| WO | WO 83/04261 | 12/1983 |
|---|---|---|
| WO | WO 2009/016275 A2 | 2/2009 |

OTHER PUBLICATIONS http://www.cbs.dtu.dk/services/SignalP/, prior to Jun. 18, 2010.
http://bmbpcu36.leeds.ac.uk/prot_analysis/Signal.htmL, prior to Jun. 18, 2010.
http://www.promega.com/vectors/mammalian_express_vectors.htm, prior to Jun. 18, 2010.
http://www.qiagen.com/overview/qiagenes.aspx?gaw=PROTQIAgenes0807&gkw=mammalian+expression, prior to Jun. 18, 2010.
http://www.scbt.com/chap_exp_vectors.php?type=pCruzTM%20Expression%20Vectors, prior to Jun. 18, 2010.
Lahaye et al., "Structure and functional properties of ulvan, a polysaccharide from green seaweeds", Biomacromolecules, 2007, vol. 8, pp. 1765-1774.
ZoBell, CE 1941, "Studies on marine bacteria. I. The cultural requirements of heterotrophic aerobes", J Mar Res 4, 41-75.
Lahaye et al., "Procédé d'extraction des ulvanes [Method of extraction of ulvans]", (1996), Hydrobiologia, 326/327, 473, English Language Abstract Only.
LaemmLi et al., "Links maturation of the head of bacteriophage T4", I. DNA packaging events, J Mol Biol, 1973, 80:575-599.
Bradford, "A rapid and sensitive method for the quantitation of microgram quantities of protein using the principle of protein-dye binding", 1976, Anal Biochem, 72:248-254.
Gacesa et al., "Plate assay for simultaneous detection of alginate lyases and determination of substrate specificity", Appl and Environ Microbiol, Jul. 1990, 56:2265-2267.
Liu et al., "Thermal Asymmetric Interlaced PCR: Automatable Amplification and Sequencing of Insert End Fragments from P1 and YAC Clones for Chromosome Walking", *Genomics*, 1995, 25:674-681.
Liu et al., "Efficient isolation and mapping of *Arabidopsis thaliana* T-DNA insert junctions by thermal asymmetric interlaced PCR", *Plant J.*, 1995, 8:457-463.
Cohen et al., "Nonchromosomal antibiotic resistance in bacteria: genetic transformation of *Escherichia coli* by R-factor DNA", Proc. Natl. Acad. Sci. USA, 1972, 69:2110-2114.
Lahaye M et al: "Fine chemical structure analysis of oligosaccharides produced by an ulvane-lyase degradation of the water-soluble cell-wall polysaccharides from *Ulva* sp." Carbohydrate Research, Pergamon, GB, vol. 304, No. 3-4, Nov. 28, 1997, pp. 325-333.
Dong Eun Kim et al: "Cloning and Characterization of Alginate Lyase from a Marine Bacterium *Streptomyces* sp. ALG-5", Marine Biotechnology, Springer-Verlag, NE, vol. 11, No. 1, Jun. 14, 2008.
Shimizu E et al: "cDNA cloning of an alginate lyase from abalone, *Hialiotis discus* hannai", Carbohydrate research, Pergamon, GB, vol. 338, No. 24, Nov. 21, 2003, pp. 2841-2852.
Zahura ua et al "an endo-beta-1,4-manninase, AkMan, from the common sea hare *Aplysia kurodai*" comparative biochemistry and physiology part B, buiochemistry and molecular biology, vol. 157, No. 1, Sep. 2010, pp. 137-143.
Barbeyron Tristan et al. *Persicivirga ulvanivorans* sp. nov., a marine member of the family Flavobacteriaceae that degrades ulvan from green algae., Int J Syst Evol Microbiol., Aug. 2011; vol. 61(Pt 8):1899-905. Epub Sep. 10, 2010.

*Primary Examiner* — Maryam Monshipouri
(74) *Attorney, Agent, or Firm* — Patterson Thuente Pedersen, P.A.

(57) ABSTRACT

The present invention notably relates to ulvan lyases, to nucleic acid sequences coding for these ulvan lyases, to vectors comprising these coding sequences, to a method of manufacturing these ulvan lyases, as well as to a method of degrading ulvans using these ulvan lyases and applicable applications to the degradation products of the ulvans. The ulvan lyases of the present invention, or ulvanolytic protein, are notably defined as proteins of 30 or 46 kD comprising the following four sequences in their peptide sequence: PNDP-NLK, LLEVGNTGTFGSTGS, DLANPDNV and WNLPE.

16 Claims, 5 Drawing Sheets

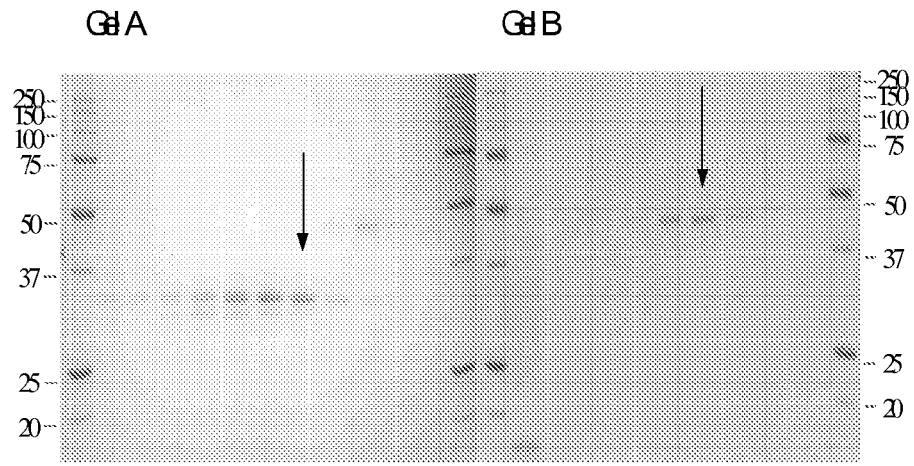

Figure 1

MVFFKDLFIFKSLIKGSLYSGHMKKKLLNYLPLFALMLFTVSMMAQTAPDEDTNSSIACP
SSGVFQNNTTRDVDIANPDNVGTVDDRTCYADYYETSVYGETWGAYNITFNSNHWDAPNT
LQPRIERSLSRSQETGVGSYARFTGTLRILEVGNTGTFGSTGSYLMQAKGKHTGGGGSND
PAICLYLARPVYGPDANGNQVQVSFDIWREQINFRGGSGAAGRTEVFLRNVLKDEIIDIE
LEVGFRQDPNDPNLKIHYSDAIIGGQVFNWNIPEPERGRESGIRYGVYRVKGGRAQMRWA
NTTYQKVEVVDNSTIPAADIYRIKNVETGEYLTSSGSSIIASTSGTGSDKEWEIISAGSG
SSYVNIDSQVRGIIRFTGGSSNPGLVSTNFSPPNTDTDKVWTVIDNNDGTVSFETRNLGR
FLYHDTNNMITHSANIDDRSKWNLESTTLSVDSQQIASVGVYPNPTVDGFTISLDNISAE
KVQIFNLLGMLVYEQKTNESSIHIDNMDNFDSGMYIISVTANDNKVYQTKLIVN

Figure 2

**ATGGTGTTTTTTAAAGATTTATTCATCTTTAAATCTTTAATTAAAGGATCTTTATATTCA
GGACACATGAAAAAAAAATTATTGAATTATTTACCATTGTTTGCATTGATGCTATTTACA
GTGTCAATGATGGCTCAAACA**GCGCCTGATGAGGATACAAATTCTAGTATAGCTTGTCCT
AGCTCAGGTGTTTTTCAAAATAATACGACTAGAGATGTAGATATAGCCAATCCTGATAAT
GTGGGTACTGTTGATGATAGAACCTGTTATGCAGATTATTATGAAACTAGTGTTTATGGA
GAAACTTGGGGAGCATATAACATAACCTTTAATTCTAATCATTGGGATGCACCTAACACA
TTACAACCTAGAATAGAGCGATCATTATCAAGGTCTCAAGAAACTGGTGTGGGAAGTTAT
GCGCGATTCACTGGGACATTGAGAATTCTTGAAGTTGGTAATACCGGTACTTTCGGTAGT
ACTGGAAGTTATCTGATGCAGGCCAAAGGTAAGCACACGGGCGGTGGTGGATCAAATGAT
CCGGCGATCTGTTTGTATTTAGCAAGACCAGTTTATGGACCTGACGCTAATGGTAATCAA
GTACAGGTATCATTTGATATTTGGAGGGAACAGATCAATTTTAGAGGTGGATCCGGAGCA
GCTGGAAGAACCGAGGTCTTTCTTAGAAATGTTTTAAAAGATGAAATAATTGATATAGAA
TTAGAAGTAGGATTTAGACAAGATCCTAATGATCCTAATTTAAAAATACACTATTCTGAT
GCTATCATAGGTGGTCAAGTATTTAATTGGAATATTCCGGAACCAGAACGAGGAAGAGAA
TCTGGTATCAGATATGGGGTTTACCGTGTAAAAGGAGGAAGAGCACAAATGAGATGGGCA
AATACGACTTATCAGAAAGTAGAAGTTGTAGATAATAGTACTATCCCTGCAGCAGATATT
TACAGGATAAAAAATGTAGAGACTGGAGAATATTTAACATCATCAGGTTCAAGCATTATC
GCAAGTACGTCAGGA<u>ACTGGTTCAGATAAAGAATGGGAGATAATCTCAGCTGGATCTGGC
TCTAGCTATGTCAATATCGATAGTCAAGTTAGAGGAATAATAAGATTTACTGGTGGATCG
TCAAATCCAGGATTAGTAAGTACAAATTTTTCACCGCCAAATACAGATACAGATAAAGTA
TGGACTGTTATTGATAATAATGATGGAACTGTTAGTTTTGAAACACGTAATCTGGGTAGG
TTTTTATATCATGATACCAATAATATGATAACACATTCAGCTAATATAGATGATAGAAGT
AAATGGAATCTTGAATCCACTACTTTAAGTGTTGATAGTCAGCAAATTGCTTCTGTAGGT
GTGTATCCTAACCCTACGGTTGATGGCTTTACaATATCCTTAGATAATATTAGTGCTGAG
AAAGTTCAAATTTTCAACCTTTTAGGAATGTTGGTATACGAACAAAAGACAAATGAGTCA
AGTATCCACATAGATAACATGGATAACTTTGATTCAGGTATGTATATCATTAGTGTCACC
GCAAATGATAACAAGGTTTATCAAACCAAGCTCATTGTAAATTAG</u>

Figure 3

SEQUENCE LISTING

```
<160> NUMBER OF SEQ ID NOS: 70

<210> SEQ ID NO 1
<211> LENGTH: 298
<212> TYPE: PRT
<213> ORGANISM: Artificial Sequence
<220> FEATURE:
<223> OTHER INFORMATION: CNCM n I-4324

<400> SEQUENCE: 1

Ala Pro Asp Glu Asp Thr Asn Ser Ser Ile Ala Cys Pro Ser Ser Gly
1               5                   10                  15

Val Phe Gln Asn Asn Thr Thr Arg Asp Val Asp Ile Ala Asn Pro Asp
```

-continued

```
                    20                  25                  30
Asn Val Gly Thr Val Asp Asp Arg Thr Cys Tyr Ala Asp Tyr Tyr Glu
            35                  40                  45
Thr Ser Val Tyr Gly Glu Thr Trp Gly Ala Tyr Asn Ile Thr Phe Asn
        50                  55                  60
Ser Asn His Trp Asp Ala Pro Asn Thr Leu Gln Pro Arg Ile Glu Arg
65                  70                  75                  80
Ser Leu Ser Arg Ser Gln Glu Thr Gly Val Gly Ser Tyr Ala Arg Phe
                85                  90                  95
Thr Gly Thr Leu Arg Ile Leu Glu Val Gly Asn Thr Gly Thr Phe Gly
            100                 105                 110
Ser Thr Gly Ser Tyr Leu Met Gln Ala Lys Gly Lys His Thr Gly Gly
        115                 120                 125
Gly Gly Ser Asn Asp Pro Ala Ile Cys Leu Tyr Leu Ala Arg Pro Val
    130                 135                 140
Tyr Gly Pro Asp Ala Asn Gly Asn Gln Val Gln Val Ser Phe Asp Ile
145                 150                 155                 160
Trp Arg Glu Gln Ile Asn Phe Arg Gly Ser Gly Ala Ala Gly Arg
                165                 170                 175
Thr Glu Val Phe Leu Arg Asn Val Leu Lys Asp Glu Ile Ile Asp Ile
            180                 185                 190
Glu Leu Glu Val Gly Phe Arg Gln Asp Pro Asn Asp Pro Asn Leu Lys
        195                 200                 205
Ile His Tyr Ser Asp Ala Ile Ile Gly Gly Val Phe Asn Trp Asn
    210                 215                 220
Ile Pro Glu Pro Glu Arg Gly Arg Glu Ser Gly Ile Arg Tyr Gly Val
225                 230                 235                 240
Tyr Arg Val Lys Gly Gly Arg Ala Gln Met Arg Trp Ala Asn Thr Thr
                245                 250                 255
Tyr Gln Lys Val Glu Val Val Asp Asn Ser Thr Ile Pro Ala Ala Asp
            260                 265                 270
Ile Tyr Arg Ile Lys Asn Val Glu Thr Gly Gly Tyr Leu Thr Ser Ser
        275                 280                 285
Gly Ser Ser Ile Ile Ala Ser Thr Ser Gly
    290                 295

<210> SEQ ID NO 2
<211> LENGTH: 189
<212> TYPE: PRT
<213> ORGANISM: Artificial Sequence
<220> FEATURE:
<223> OTHER INFORMATION: CNCM n I-4324

<400> SEQUENCE: 2

Thr Gly Ser Asp Lys Glu Trp Glu Ile Ile Ser Ala Gly Ser Gly Ser
1               5                   10                  15
Ser Tyr Val Asn Ile Asp Ser Gln Val Arg Gly Ile Ile Arg Phe Thr
                20                  25                  30
Gly Gly Ser Ser Asn Pro Gly Leu Val Ser Thr Asn Phe Ser Pro Pro
            35                  40                  45
Asn Thr Asp Thr Asp Lys Val Trp Thr Val Ile Asp Asn Asn Asp Gly
        50                  55                  60
Thr Val Ser Phe Glu Thr Arg Asn Leu Gly Arg Phe Leu Tyr His Asp
65                  70                  75                  80
Thr Asn Asn Met Ile Thr His Ser Ala Asn Ile Asp Asp Arg Ser Lys
                85                  90                  95
```

```
Trp Asn Leu Glu Ser Thr Thr Leu Ser Val Asp Ser Gln Gln Ile Ala
            100                 105                 110

Ser Val Gly Val Tyr Pro Asn Pro Thr Val Asp Gly Phe Thr Ile Ser
            115                 120                 125

Leu Asp Asn Ile Ser Ala Glu Lys Val Gln Ile Phe Asn Leu Leu Gly
            130                 135                 140

Met Leu Val Tyr Glu Gln Lys Thr Asn Glu Ser Ser Ile His Ile Asp
145                 150                 155                 160

Asn Met Asp Asn Phe Asp Ser Gly Met Tyr Ile Ile Ser Val Thr Ala
                165                 170                 175

Asn Asp Asn Lys Val Tyr Gln Thr Lys Leu Ile Val Asn
            180                 185

<210> SEQ ID NO 3
<211> LENGTH: 47
<212> TYPE: PRT
<213> ORGANISM: Artificial Sequence
<220> FEATURE:
<223> OTHER INFORMATION: CNCM n I-4324

<400> SEQUENCE: 3

Met Val Phe Phe Lys Asp Leu Phe Ile Phe Lys Ser Leu Ile Lys Gly
1               5                   10                  15

Ser Leu Tyr Ser Gly His Met Lys Lys Lys Leu Leu Asn Tyr Leu Pro
            20                  25                  30

Leu Phe Ala Leu Met Leu Phe Thr Val Ser Met Met Ala Gln Thr
            35                  40                  45

<210> SEQ ID NO 4
<211> LENGTH: 534
<212> TYPE: PRT
<213> ORGANISM: Artificial Sequence
<220> FEATURE:
<223> OTHER INFORMATION: CNCM n I-4324

<400> SEQUENCE: 4

Met Val Phe Phe Lys Asp Leu Phe Ile Phe Lys Ser Leu Ile Lys Gly
1               5                   10                  15

Ser Leu Tyr Ser Gly His Met Lys Lys Lys Leu Leu Asn Tyr Leu Pro
            20                  25                  30

Leu Phe Ala Leu Met Leu Phe Thr Val Ser Met Met Ala Gln Thr Ala
            35                  40                  45

Pro Asp Glu Asp Thr Asn Ser Ser Ile Ala Cys Pro Ser Ser Gly Val
            50                  55                  60

Phe Gln Asn Asn Thr Thr Arg Asp Val Asp Ile Ala Asn Pro Asp Asn
65                  70                  75                  80

Val Gly Thr Val Asp Asp Arg Thr Cys Tyr Ala Asp Tyr Tyr Glu Thr
            85                  90                  95

Ser Val Tyr Gly Glu Thr Trp Gly Ala Tyr Asn Ile Thr Phe Asn Ser
            100                 105                 110

Asn His Trp Asp Ala Pro Asn Thr Leu Gln Pro Arg Ile Glu Arg Ser
            115                 120                 125

Leu Ser Arg Ser Gln Glu Thr Gly Val Gly Ser Tyr Ala Arg Phe Thr
            130                 135                 140

Gly Thr Leu Arg Ile Leu Glu Val Gly Asn Thr Gly Thr Phe Gly Ser
145                 150                 155                 160

Thr Gly Ser Tyr Leu Met Gln Ala Lys Gly Lys His Thr Gly Gly Gly
                165                 170                 175
```

Gly Ser Asn Asp Pro Ala Ile Cys Leu Tyr Leu Ala Arg Pro Val Tyr
            180                 185                 190

Gly Pro Asp Ala Asn Gly Asn Gln Val Gln Val Ser Phe Asp Ile Trp
        195                 200                 205

Arg Glu Gln Ile Asn Phe Arg Gly Gly Ser Gly Ala Ala Gly Arg Thr
    210                 215                 220

Glu Val Phe Leu Arg Asn Val Leu Lys Asp Glu Ile Ile Asp Ile Glu
225                 230                 235                 240

Leu Glu Val Gly Phe Arg Gln Asp Pro Asn Asp Pro Asn Leu Lys Ile
            245                 250                 255

His Tyr Ser Asp Ala Ile Ile Gly Gly Gln Val Phe Asn Trp Asn Ile
        260                 265                 270

Pro Glu Pro Glu Arg Gly Arg Glu Ser Gly Ile Arg Tyr Gly Val Tyr
    275                 280                 285

Arg Val Lys Gly Gly Arg Ala Gln Met Arg Trp Ala Asn Thr Thr Tyr
290                 295                 300

Gln Lys Val Glu Val Val Asp Asn Ser Thr Ile Pro Ala Ala Asp Ile
305                 310                 315                 320

Tyr Arg Ile Lys Asn Val Glu Thr Gly Glu Tyr Leu Thr Ser Ser Gly
            325                 330                 335

Ser Ser Ile Ile Ala Ser Thr Ser Gly Thr Gly Ser Asp Lys Glu Trp
        340                 345                 350

Glu Ile Ile Ser Ala Gly Ser Gly Ser Ser Tyr Val Asn Ile Asp Ser
    355                 360                 365

Gln Val Arg Gly Ile Ile Arg Phe Thr Gly Gly Ser Ser Asn Pro Gly
370                 375                 380

Leu Val Ser Thr Asn Phe Ser Pro Pro Asn Thr Asp Thr Asp Lys Val
385                 390                 395                 400

Trp Thr Val Ile Asp Asn Asn Asp Gly Thr Val Ser Phe Glu Thr Arg
            405                 410                 415

Asn Leu Gly Arg Phe Leu Tyr His Asp Thr Asn Asn Met Ile Thr His
        420                 425                 430

Ser Ala Asn Ile Asp Asp Arg Ser Lys Trp Asn Leu Glu Ser Thr Thr
    435                 440                 445

Leu Ser Val Asp Ser Gln Gln Ile Ala Ser Val Gly Val Tyr Pro Asn
450                 455                 460

Pro Thr Val Asp Gly Phe Thr Ile Ser Leu Asp Asn Ile Ser Ala Glu
465                 470                 475                 480

Lys Val Gln Ile Phe Asn Leu Leu Gly Met Leu Val Tyr Glu Gln Lys
            485                 490                 495

Thr Asn Glu Ser Ser Ile His Ile Asp Asn Met Asp Asn Phe Asp Ser
        500                 505                 510

Gly Met Tyr Ile Ile Ser Val Thr Ala Asn Asp Asn Lys Val Tyr Gln
    515                 520                 525

Thr Lys Leu Ile Val Asn
    530

<210> SEQ ID NO 5
<211> LENGTH: 896
<212> TYPE: DNA
<213> ORGANISM: Artificial Sequence
<220> FEATURE:
<223> OTHER INFORMATION: CNCM n I-4324

<400> SEQUENCE: 5

```
gcgcctgatg aggatacaaa ttctagtata gcttgtccta gctcaggtgt ttttcaaaat    60
aatacgacta gagatgtaga tatagccaat cctgataatg tgggtactgt tgatgataga   120
acctgttatg cagattatta tgaaactagt gtttatggag aaacttgggg agcatataac   180
ataaccttta attctaatca ttgggatgca cctaacacat tacaacctag aatagagcga   240
tcattatcaa ggtctcaaga aactggtgtg ggaagttatg cgcgattcac tgggacattg   300
agaattcttg aagttggtaa taccggtact ttcggtagta ctggaagtta tctgatgcag   360
gccaaaggta agcacacggg cggtggtgga tcaaatgatc cggcgatctg tttgtattta   420
gcaagaccag tttatggacc tgacgctaat ggtaatcaag tacaggtatc atttgatatt   480
tggagggaac agatcaattt tagaggtgga tccggagcag ctggaagaac cgaggtcttt   540
cttagaaatg ttttaaaaga tgaaataatt gatatagaat tagaagtagg atttagacaa   600
gatcctaatg atcctaattt aaaaatacac tattctgatg ctatcatagg tggtcaagta   660
tttaattgga atattccgga accagaacga ggaagagaat ctggtatcag atatggggtt   720
taccgtgtaa aaggaggaag agcacaaatg agatgggcaa atacgactta tcagaaagta   780
gaagttgtag ataatagtac tatccctgca gcagatattt acaggataaa aaatgtagag   840
actggagaat atttaacatc atcaggttca agcattatcg caagtacgtc aggaac       896
```

`<210> SEQ ID NO 6`
`<211> LENGTH: 569`
`<212> TYPE: DNA`
`<213> ORGANISM: Artificial Sequence`
`<220> FEATURE:`
`<223> OTHER INFORMATION: CNCM n I-4324`

`<400> SEQUENCE: 6`

```
actggttcag ataagaatg ggagataatc tcagctggat ctggctctag ctatgtcaat     60
atcgatagtc aagttagagg aataataaga tttactggtg gatcgtcaaa tccaggatta   120
gtaagtacaa attttcacc gccaaataca gatacagata agtatggac tgttattgat    180
aataatgatg aactgttag ttttgaaaca cgtaatctgg gtaggttttt atatcatgat    240
accaataata tgataacaca ttcagctaat atagatgata gaagtaaatg gaatcttgaa   300
tccactactt taagtgttga tagtcagcaa attgcttctg taggtgtgta tcctaaccct   360
acggttgatg gctttacaat atccttagat aatattagtc tgagaaagt tcaaatttc   420
aacctttag gaatgttggt atacgaacaa aagacaaatg agtcaagtat ccacatagat   480
aacatggata ctttgattc aggtatgtat atcattagtg tcaccgcaaa tgataacaag   540
gtttatcaaa ccaagctcat tgtaaatta                                   569
```

`<210> SEQ ID NO 7`
`<211> LENGTH: 143`
`<212> TYPE: DNA`
`<213> ORGANISM: Artificial Sequence`
`<220> FEATURE:`
`<223> OTHER INFORMATION: CNCM n I-4324`

`<400> SEQUENCE: 7`

```
atggtgtttt ttaaagattt attcatcttt aaatctttaa ttaaaggatc tttatattca    60
ggacacatga aaaaaaaatt attgaattat ttaccattgt ttgcattgat gctatttaca   120
gtgtcaatga tggctcaaac agc                                          143
```

`<210> SEQ ID NO 8`
`<211> LENGTH: 1607`
`<212> TYPE: DNA`

<213> ORGANISM: Artificial Sequence
<220> FEATURE:
<223> OTHER INFORMATION: CNCM n I-4324

<400> SEQUENCE: 8

```
atggtgtttt ttaaagattt attcatcttt aaatctttaa ttaaaggatc tttatattca      60
ggacacatga aaaaaaaatt attgaattat ttaccattgt ttgcattgat gctatttaca     120
gtgtcaatga tggctcaaac agcgcgcctg atgaggatac aaattctagt atagcttgtc     180
ctagctcagg tgtttttcaa aataatacga ctagagatgt agatatagcc aatcctgata     240
atgtgggtac tgttgatgat agaacctgtt atgcagatta ttatgaaact agtgtttatg     300
gagaaacttg gggagcatat aacataacct ttaattctaa tcattgggat gcacctaaca     360
cattacaacc tagaatagag cgatcattat caaggtctca agaaactggt gtgggaagtt     420
atgcgcgatt cactgggaca ttgagaattc ttgaagttgg taataccggt actttcggta     480
gtactggaag ttatctgatg caggccaaag gtaagcacac gggcggtggt ggatcaaatg     540
atccggcgat ctgtttgtat ttagcaagac cagtttatgg acctgacgct aatggtaatc     600
aagtacaggt atcatttgat atttggaggg aacagatcaa ttttagaggt ggatccggag     660
cagctggaag aaccgaggtc tttcttagaa atgttttaaa agatgaaata attgatatag     720
aattagaagt aggatttaga caagatccta atgatcctaa tttaaaaata cactattctg     780
atgctatcat aggtggtcaa gtatttaatt ggaatattcc ggaaccagaa cgaggaagag     840
aatctggtat cagatatggg gtttaccgtg taaaggagg aagagcacaa atgagatggg     900
caaatacgac ttatcagaaa gtagaagttg tagataatag tactatccct gcagcagata     960
tttacaggat aaaaaatgta gagactggag aatatttaac atcatcaggt tcaagcatta    1020
tcgcaagtac gtcaggaact ggttcagata agaatggga gataatctca gctggatctg    1080
gctctagcta tgtcaatatc gatagtcaag ttagaggaat aataagattt actggtggat    1140
cgtcaaatcc aggattagta agtacaaatt tttcaccgcc aaatacagat acagataaag    1200
tatggactgt tattgataat aatgatgaa ctgttagttt tgaaacacgt aatctgggta    1260
ggttttata tcatgatacc aataaatga taacacattc agctaatata gatgatagaa    1320
gtaaatggaa tcttgaatcc actactttaa gtgttgatag tcagcaaatt gcttctgtag    1380
gtgtgtatcc taaccctacg gttgatggct ttacaatatc cttagataat attagtgctg    1440
agaaagttca aattttcaac cttttaggaa tgttggtata cgaacaaaag acaaatgagt    1500
caagtatcca catagataac atggataact ttgattcagg tatgtatatc attagtgtca    1560
ccgcaaatga taacaaggtt tatcaaacca agctcattgt aaaattag               1607
```

<210> SEQ ID NO 9
<211> LENGTH: 7
<212> TYPE: PRT
<213> ORGANISM: Artificial Sequence
<220> FEATURE:
<223> OTHER INFORMATION: CNCM n I-4324

<400> SEQUENCE: 9

Pro Asn Asp Pro Asn Leu Lys
1               5

<210> SEQ ID NO 10
<211> LENGTH: 15
<212> TYPE: PRT
<213> ORGANISM: Artificial Sequence
<220> FEATURE:
<223> OTHER INFORMATION: CNCM n I-4324

```
<400> SEQUENCE: 10

Leu Leu Glu Val Gly Asn Thr Gly Thr Phe Gly Ser Thr Gly Ser
1               5                   10                  15

<210> SEQ ID NO 11
<211> LENGTH: 8
<212> TYPE: PRT
<213> ORGANISM: Artificial Sequence
<220> FEATURE:
<223> OTHER INFORMATION: CNCM n I-4324

<400> SEQUENCE: 11

Asp Leu Ala Asn Pro Asp Asn Val
1               5

<210> SEQ ID NO 12
<211> LENGTH: 14
<212> TYPE: PRT
<213> ORGANISM: Artificial Sequence
<220> FEATURE:
<223> OTHER INFORMATION: CNCM n I-4324

<400> SEQUENCE: 12

Ala Leu Leu Gly Gly Gln Val Phe Asn Trp Asn Leu Pro Glu
1               5                   10

<210> SEQ ID NO 13
<211> LENGTH: 17
<212> TYPE: PRT
<213> ORGANISM: Artificial Sequence
<220> FEATURE:
<223> OTHER INFORMATION: CNCM n I-4324

<400> SEQUENCE: 13

Asx Leu Leu Glu Val Gly Asn Thr Gly Thr Phe Gly Ser Thr Gly Ser
1               5                   10                  15

Ala

<210> SEQ ID NO 14
<211> LENGTH: 15
<212> TYPE: PRT
<213> ORGANISM: Artificial Sequence
<220> FEATURE:
<223> OTHER INFORMATION: CNCM n I-4324

<400> SEQUENCE: 14

Ala Leu Leu Gly Gly Gln Val Phe Asn Trp Asn Leu Pro Glu Ser
1               5                   10                  15

<210> SEQ ID NO 15
<211> LENGTH: 7
<212> TYPE: PRT
<213> ORGANISM: Artificial Sequence
<220> FEATURE:
<223> OTHER INFORMATION: CNCM n I-4324

<400> SEQUENCE: 15

Asx Glu Gln Leu Asn Phe Arg
1               5

<210> SEQ ID NO 16
<211> LENGTH: 9
<212> TYPE: PRT
<213> ORGANISM: Artificial Sequence
<220> FEATURE:
<223> OTHER INFORMATION: CNCM n I-4324
```

-continued

```
<400> SEQUENCE: 16

Leu Glu Leu Leu Asp Leu Glu Leu Glu
1               5

<210> SEQ ID NO 17
<211> LENGTH: 8
<212> TYPE: PRT
<213> ORGANISM: Artificial Sequence
<220> FEATURE:
<223> OTHER INFORMATION: CNCM n I-4324

<400> SEQUENCE: 17

Thr Gly Val Gly Ser Tyr Ala Arg
1               5

<210> SEQ ID NO 18
<211> LENGTH: 16
<212> TYPE: PRT
<213> ORGANISM: Artificial Sequence
<220> FEATURE:
<223> OTHER INFORMATION: CNCM n I-4324

<400> SEQUENCE: 18

Asx Pro Val Tyr Gly Asn Gln Val Gln Val Ser Phe Asp Leu Trp Arg
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: CNCM n I-4324

<400> SEQUENCE: 19

Gly Gly Gly Gly Ser Asn Asp Pro Ala Leu Cys Leu Tyr Leu Ala Arg
1               5                   10                  15

<210> SEQ ID NO 20
<211> LENGTH: 9
<212> TYPE: PRT
<213> ORGANISM: Artificial Sequence
<220> FEATURE:
<223> OTHER INFORMATION: CNCM n I-4324

<400> SEQUENCE: 20

Ala Cys Pro Ser Ser Gly Val Phe Gln
1               5

<210> SEQ ID NO 21
<211> LENGTH: 6
<212> TYPE: PRT
<213> ORGANISM: Artificial Sequence
<220> FEATURE:
<223> OTHER INFORMATION: CNCM n I-4324

<400> SEQUENCE: 21

Leu Leu Ser Gly Trp Gly
1               5

<210> SEQ ID NO 22
<211> LENGTH: 8
<212> TYPE: PRT
<213> ORGANISM: Artificial Sequence
<220> FEATURE:
<223> OTHER INFORMATION: CNCM n I-4324

<400> SEQUENCE: 22
```

Asx Val Tyr Asp Asn Thr Leu Val
1               5

<210> SEQ ID NO 23
<211> LENGTH: 8
<212> TYPE: PRT
<213> ORGANISM: Artificial Sequence
<220> FEATURE:
<223> OTHER INFORMATION: CNCM n I-4324

<400> SEQUENCE: 23

Phe Gly Val Thr Gly Pro Pro Thr
1               5

<210> SEQ ID NO 24
<211> LENGTH: 8
<212> TYPE: PRT
<213> ORGANISM: Artificial Sequence
<220> FEATURE:
<223> OTHER INFORMATION: CNCM n I-4324

<400> SEQUENCE: 24

Asp Leu Leu Gly Asn Thr Leu Asp
1               5

<210> SEQ ID NO 25
<211> LENGTH: 9
<212> TYPE: PRT
<213> ORGANISM: Artificial Sequence
<220> FEATURE:
<223> OTHER INFORMATION: CNCM n I-4324

<400> SEQUENCE: 25

Asx Asp Thr Asp Leu Pro Asn Pro Arg
1               5

<210> SEQ ID NO 26
<211> LENGTH: 5
<212> TYPE: PRT
<213> ORGANISM: Artificial Sequence
<220> FEATURE:
<223> OTHER INFORMATION: CNCM n I-4324

<400> SEQUENCE: 26

Ala Thr Gly Ala Gly
1               5

<210> SEQ ID NO 27
<211> LENGTH: 15
<212> TYPE: PRT
<213> ORGANISM: Artificial Sequence
<220> FEATURE:
<223> OTHER INFORMATION: CNCM n I-4324

<400> SEQUENCE: 27

Asx Ser Cys Tyr Ala Asn Tyr Ser Glu Ser Ser Leu Leu Gly Lys
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: CNCM n I-4324

<400> SEQUENCE: 28

Asx Asp Asp Pro Asn Asn Pro Gly Gln Thr Leu His Tyr Ala Trp Lys

-continued

```
<210> SEQ ID NO 29
<211> LENGTH: 10
<212> TYPE: PRT
<213> ORGANISM: Artificial Sequence
<220> FEATURE:
<223> OTHER INFORMATION: CNCM n I-4324

<400> SEQUENCE: 29

Asx Phe Trp Gly Leu Tyr Asn Leu Thr Asp
1               5                   10

<210> SEQ ID NO 30
<211> LENGTH: 21
<212> TYPE: PRT
<213> ORGANISM: Artificial Sequence
<220> FEATURE:
<223> OTHER INFORMATION: CNCM n I-4324

<400> SEQUENCE: 30

Leu Leu Glu Val Gly Asn Thr Gly Thr Phe Gly Ser Thr Gly Ser Tyr
1               5                   10                  15

Leu Met Gln Ala Lys
            20

<210> SEQ ID NO 31
<211> LENGTH: 14
<212> TYPE: PRT
<213> ORGANISM: Artificial Sequence
<220> FEATURE:
<223> OTHER INFORMATION: CNCM n I-4324

<400> SEQUENCE: 31

Asp Leu Ala Asn Pro Asp Asn Val Gly Thr Val Asp Asp Arg
1               5                   10

<210> SEQ ID NO 32
<211> LENGTH: 16
<212> TYPE: PRT
<213> ORGANISM: Artificial Sequence
<220> FEATURE:
<223> OTHER INFORMATION: CNCM n I-4324

<400> SEQUENCE: 32

Gln Glu Met Ala Leu Leu Met Gln Glu Val Asp Trp Asn Leu Pro Glu
1               5                   10                  15

<210> SEQ ID NO 33
<211> LENGTH: 5
<212> TYPE: PRT
<213> ORGANISM: Artificial Sequence
<220> FEATURE:
<223> OTHER INFORMATION: CNCM n I-4324

<400> SEQUENCE: 33

Ala Asp Leu Tyr Arg
1               5

<210> SEQ ID NO 34
<211> LENGTH: 14
<212> TYPE: PRT
<213> ORGANISM: Artificial Sequence
<220> FEATURE:
<223> OTHER INFORMATION: CNCM n I-4324

<400> SEQUENCE: 34
```

Val Val Asp Asn Ser Thr Leu Pro Ala Ala Asp Leu Tyr Arg
1               5                   10

<210> SEQ ID NO 35
<211> LENGTH: 5
<212> TYPE: PRT
<213> ORGANISM: Artificial Sequence
<220> FEATURE:
<223> OTHER INFORMATION: CNCM n I-4324

<400> SEQUENCE: 35

Ala Asp Leu Tyr Arg
1               5

<210> SEQ ID NO 36
<211> LENGTH: 17
<212> TYPE: PRT
<213> ORGANISM: Artificial Sequence
<220> FEATURE:
<223> OTHER INFORMATION: CNCM n I-4324

<400> SEQUENCE: 36

Tyr His Asp Thr Asn Asn Met Leu Thr His Ser Ala Asn Leu Asp Asp
1               5                   10                  15

Arg

<210> SEQ ID NO 37
<211> LENGTH: 12
<212> TYPE: PRT
<213> ORGANISM: Artificial Sequence
<220> FEATURE:
<223> OTHER INFORMATION: CNCM n I-4324

<400> SEQUENCE: 37

Leu Tyr Glu Asn Gly Glu Leu Val Asp Glu Phe Leu
1               5                   10

<210> SEQ ID NO 38
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 38
gtnggnaaya cnggnacntt ygg                                   23

<210> SEQ ID NO 39
<211> LENGTH: 20
<212> TYPE: DNA

```
<213> ORGANISM: Artificial Sequence
<220> FEATURE:
<223> OTHER INFORMATION: Amorce
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 39
ccnaaygayc cnaayytnaa                                              20

<210> SEQ ID NO 40
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 40
gcnaayccng ayaaygtngg                                              20

<210> SEQ ID NO 41
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 41
acnytnccng cngcngayyt nta                                          23
```

```
<210> SEQ ID NO 42
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 42
ggnggncarg tnttyaaytg g                                              21

<210> SEQ ID NO 43
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 43
ggncaracny tncaytaygc ntgg                                           24

<210> SEQ ID NO 44
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
```

```
<400> SEQUENCE: 44
ccraangtnc cngtrttncc nac                                                    23

<210> SEQ ID NO 45
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 45
ttnarrttng grtcrttngg                                                        20

<210> SEQ ID NO 46
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 46
ccnacrttrt cnggrttngc                                                        20

<210> SEQ ID NO 47
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
```

<221> NAME/KEY: misc_feature
<222> LOCATION: (21)..(21)
<223> OTHER INFORMATION: n is a, c, g, or t

<400> SEQUENCE: 47
tanarrtcng cngcnggnar ngt                                           23

<210> SEQ ID NO 48
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 48
ccarttraan acytgnccnc c                                             21

<210> SEQ ID NO 49
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 49
ccangcrtar tgnarngtyt gncc                                          24

<210> SEQ ID NO 50
<211> LENGTH: 28
<212> TYPE: DNA
<213> ORGANISM: Artificial Sequence
<220> FEATURE:
<223> OTHER INFORMATION: Primer

<400> SEQUENCE: 50
ctaggttgta atgtgttagg tgcatccc                                      28

<210> SEQ ID NO 51
<211> LENGTH: 26
<212> TYPE: DNA
<213> ORGANISM: Artificial Sequence
<220> FEATURE:
<223> OTHER INFORMATION: Primer

```
<400> SEQUENCE: 51
gtgaatcgcg cataacttcc cacacc                                         26

<210> SEQ ID NO 52
<211> LENGTH: 24
<212> TYPE: DNA
<213> ORGANISM: Artificial Sequence
<220> FEATURE:
<223> OTHER INFORMATION: Primer

<400> SEQUENCE: 52
cccgtgtgct tacctttggc ctgc                                           24

<210> SEQ ID NO 53
<211> LENGTH: 25
<212> TYPE: DNA
<213> ORGANISM: Artificial Sequence
<220> FEATURE:
<223> OTHER INFORMATION: Primer

<400> SEQUENCE: 53
gcagctggaa gaaccgaggt ctttc                                          25

<210> SEQ ID NO 54
<211> LENGTH: 26
<212> TYPE: DNA
<213> ORGANISM: Artificial Sequence
<220> FEATURE:
<223> OTHER INFORMATION: Primer

<400> SEQUENCE: 54
ccggaaccag aacgaggaag agaatc                                         26

<210> SEQ ID NO 55
<211> LENGTH: 26
<212> TYPE: DNA
<213> ORGANISM: Artificial Sequence
<220> FEATURE:
<223> OTHER INFORMATION: Primer

<400> SEQUENCE: 55
ggaggaagag cacaaatgag atgggc                                         26

<210> SEQ ID NO 56
<211> LENGTH: 35
<212> TYPE: DNA
<213> ORGANISM: Artificial Sequence
<220> FEATURE:
<223> OTHER INFORMATION: Primer

<400> SEQUENCE: 56
cacgtaatct gggtaggttt ttatatcatg atacc                               35

<210> SEQ ID NO 57
<211> LENGTH: 26
<212> TYPE: DNA
<213> ORGANISM: Artificial Sequence
<220> FEATURE:
<223> OTHER INFORMATION: Primer

<400> SEQUENCE: 57
gcttctgtag gtgtgtatcc taaccc                                         26

<210> SEQ ID NO 58
<211> LENGTH: 29
<212> TYPE: DNA
```

<213> ORGANISM: Artificial Sequence
<220> FEATURE:
<223> OTHER INFORMATION: Primer

<400> SEQUENCE: 58
gctggacgtg tgtcttcttt gtattacgc                                    29

<210> SEQ ID NO 59
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 59
tgwgnagwan casaga                                                  16

<210> SEQ ID NO 60
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 60
agwgnagwan cawagg                                                  16

<210> SEQ ID NO 61
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 61
wgtgnagwan canaga                                                  16

<210> SEQ ID NO 62
<211> LENGTH: 15
<212> TYPE: DNA
<213> ORGANISM: Artificial Sequence
<220> FEATURE:
<223> OTHER INFORMATION: Primer
<220> FEATURE:

-continued

```
<221> NAME/KEY: misc_feature
<222> LOCATION: (1)..(1)
<223> OTHER INFORMATION: n is a, c, g, or t

<400> SEQUENCE: 62
ntcgastwts gwgtt                                                        15

<210> SEQ ID NO 63
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 63
ngtcgaswga nawgaa                                                       16

<210> SEQ ID NO 64
<211> LENGTH: 8
<212> TYPE: PRT
<213> ORGANISM: Artificial Sequence
<220> FEATURE:
<223> OTHER INFORMATION: CNCM n I-4324

<400> SEQUENCE: 64

Val Gly Asn Thr Gly Thr Phe Gly
1               5

<210> SEQ ID NO 65
<211> LENGTH: 7
<212> TYPE: PRT
<213> ORGANISM: Artificial Sequence
<220> FEATURE:
<223> OTHER INFORMATION: CNCM n I-4324

<400> SEQUENCE: 65

Ala Asn Pro Asp Asn Val Gly
1               5

<210> SEQ ID NO 66
<211> LENGTH: 8
<212> TYPE: PRT
<213> ORGANISM: Artificial Sequence
<220> FEATURE:
<223> OTHER INFORMATION: CNCM n I-4324

<400> SEQUENCE: 66

Thr Leu Pro Ala Ala Asp Leu Tyr
1               5

<210> SEQ ID NO 67
<211> LENGTH: 7
<212> TYPE: PRT
<213> ORGANISM: Artificial Sequence
<220> FEATURE:
<223> OTHER INFORMATION: CNCM n I-4324

<400> SEQUENCE: 67

Gly Gly Gln Val Phe Asn Trp
1               5
```

```
<210> SEQ ID NO 68
<211> LENGTH: 8
<212> TYPE: PRT
<213> ORGANISM: Artificial Sequence
<220> FEATURE:
<223> OTHER INFORMATION: CNCM n I-4324

<400> SEQUENCE: 68

Gly Gln Thr Leu His Tyr Ala Trp
1               5

<210> SEQ ID NO 69
<211> LENGTH: 36
<212> TYPE: DNA
<213> ORGANISM: Artificial Sequence
<220> FEATURE:
<223> OTHER INFORMATION: CNCM I 4324

<400> SEQUENCE: 69 gggggagat ctgcgcctga tgaggataca aattct                36

<210> SEQ ID NO 70
<211> LENGTH: 39
<212> TYPE: DNA
<213> ORGANISM: Artificial Sequence
<220> FEATURE:
<223> OTHER INFORMATION: CNCM I 4324

<400> SEQUENCE: 70 ccccccaat tgttatcctg acgtacttgc gataatgct             39
```

ULVAN LYASE, METHOD FOR MANUFACTURING SAME, AND USES THEREOF

RELATED APPLICATIONS

The present application is a National Phase entry of PCT Application No. PCT/FR2011/051384, filed Jun. 16, 2011, which claims priority from France Application No. 1002588, filed Jun. 18, 2010, the disclosures of which are hereby incorporated by reference in their entireties.

TECHNICAL FIELD

The present invention notably relates to ulvan lyases, to nucleic acid coding sequences for these ulvan lyases, to vectors comprising these coding sequences, to a method of manufacturing these ulvan lyases, as well as to a method of degrading ulvans using these ulvan lyases.

The present invention notably finds applications in valorization of natural bioresources consisting of organisms and microorganisms comprising ulvans, notably green algae. In particular, it finds applications in the laboratory, for analysis of these ulvans, as well as in food processing, in the area of cosmetics and in the area of medicinal products and pharmaceutical formulations, where the products of degradation of ulvans can be utilized.

In the following description, references in square brackets [ ] refer to the list of references given at the end of the text.

BACKGROUND OF THE INVENTION

The green algae belonging to the order Ulvales (*Ulva* sp. and *Enteromorpha* sp.) are present everywhere on Earth and are very commonly encountered on coasts. These algae are frequently involved in algal blooms promoted by eutrophication of coastal waters, giving rise to "green tides".

Until now this undesirable biomass has been of very low added value and it is used essentially as compost.

The anionic complex polysaccharides present in the cell walls of the ulvales, called ulvans, possess unusual structures and represent a source of biopolymers whose functionalities have so far received little attention.

The ulvans are made up of various disaccharide repeating units constructed with rhamnose units, glucuronic acids, iduronic acids, xyloses and sulphates. The two main repeating units are called aldobiuronic acid, or ulvanobiuronic acids, or A ($A_{3S}$) and B ($B_{3S}$) respectively, which have the following formulae:

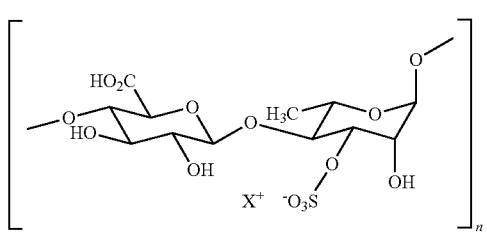

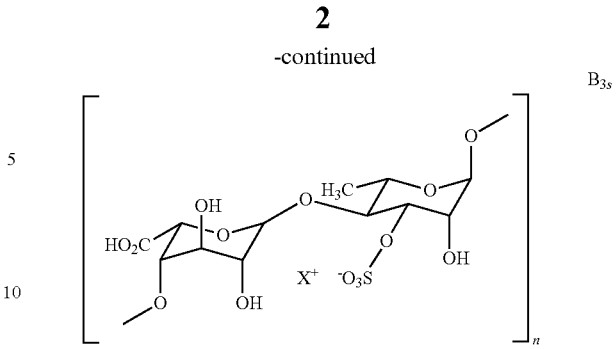

The A unit ($A_{3S}$) is beta-D-1,4-glucuronic acid (1→4) alpha-L-1,4-rhamnose 3-sulphate. The B unit ($B_{3S}$) is alpha-L-1,4-iduronic acid (1→4) alpha-L-1,4-rhamnose 3-sulphate.

The uronic acids are sometimes replaced with xylose residues sulphated to O-2.

The ulvans possess unique physicochemical properties that make them attractive candidates for new food-industry, pharmaceutical, and cosmetic applications. The ulvans possess very unusual structures composed of rare sugars or monosaccharides such as rhamnose and iduronic acid. Rhamnose is an important compound of the surface antigens of numerous microorganisms that are recognized specifically by mammalian lectins. It is also used for the synthesis of flavouring materials. Iduronic acid is used for the synthesis of glycosaminoglycans, for example heparin.

In addition to the monomers, the ulvans and oligo-ulvans have interesting biological properties. In fact, studies have shown, for example, that oligo-ulvans have antitumour, antiviral, notably anti-influenzal, and anticoagulant activities. A non-exhaustive list of potential applications of the ulvans was proposed by M. Lahaye and A. Robic in the document Structure and functional properties of ulvan, a polysaccharide from green seaweeds. Biomacromolecules 2007, 8, 1765-1774 [1].

In this context, better understanding of the structure of the ulvans and the development of methods for fragmenting the ulvans in oligomeric or monomeric form are of considerable interest.

At present, through lack of means for understanding them better and for degrading them efficiently, the algae, notably the green algae, are essentially composted, without any industrial utilization. This is all the more deplorable since it is an abundant source, which is sometimes troublesome in terms of pollution of our maritime coastlines. At present they are eliminated of by composting.

There is therefore a real need to find novel means of degradation of ulvans so as to be able to valorize this bioresource, obtained notably from green algae, producing "tailor-made" oligo-ulvan fragments in view of cosmetic, food-processing and medical applications.

SUMMARY OF THE INVENTION

The aim of the present invention is precisely to meet this need by supplying ulvan lyases that degrade ulvans very effectively by depolymerization. Investigation of the conditions for recognition of the enzymes of the present invention undertaken by the inventors demonstrates their glucuronic lyase activity.

The inventors have also demonstrated iduronic and glucuronic lyase activity.

The inventors supply, in particular, ulvan lyases extracted from the microorganism deposited under number I-4324 in the National Collection of Cultures of Microorganisms (CNCM) 25 rue du docteur Roux, 75724 Paris Cedex 15, France. This microorganism is also called "01-PN-2010" in the present text and in the CNCM deposition documents.

In other words, the inventors supply, in particular, ulvan lyases extracted from the microorganism of marine origin deposited under number I-4324 in the National Collection of Cultures of Microorganisms (CNCM) 25 rue du docteur Roux, 75724 Paris Cedex 15, France.

These ulvan lyases, also called ulvanolytic proteins, can be for example of 30 or 46 kD and can comprise the following four sequences in their peptide sequence:

PNDPNLK, (SEQ ID No. 9)

LLEVGNTGTFGSTGS, (SEQ ID No. 10)

DLANPDNV, (SEQ ID No. 11)
and

WNLPE. (SEQ ID No. 12)

In some aspects of the present invention, ulvan lyase of 30 or 46 kD are of sequence SEQ ID No. 1 in the appended sequence listing. This ulvan lyase may further comprise at its C-terminal end, the sequence SEQ ID No. 2 in the appended sequence listing. In some aspects the ulvan lyase further has a signal sequence at its N-terminal end. In some aspects, the signal sequence is the sequence SEQ ID No. 3 in the appended sequence listing.

The present invention also relates to nucleic acids coding for the ulvan lyases of the present invention, notably for the protein SEQ ID No. 1. It can be for example a nucleic acid comprising or consisting of the sequence SEQ ID No. 5 in the appended sequence listing. In some aspects, the nucleic acid comprises at its 3' end the sequence SEQ ID No. 6 in the appended sequence listing. In some aspects, the nucleic acid comprises at its 5' end the sequence SEQ ID No. 7 in the appended sequence listing.

The present invention also relates to a vector comprising a nucleic acid coding for one of the ulvan lyases of the present invention. In some aspects, the vector comprises a nucleic acid selected from the sequences SEQ ID No. 5 to 8 in the appended sequence listing.

The present invention also relates to a host cell comprising a nucleic acid sequence according to the present invention or a vector according to the present invention.

The present invention also relates to an isolated marine bacterium microorganism, which is named 01-PN-2010, which produces the ulvan lyases of the present invention, the isolated bacterium deposited on 17 Jun. 2010 under number I-4324 in the National Collection of Cultures of Microorganisms (CNCM) 25 rue du docteur Roux, 75724 Paris Cedex 15, France.

The present invention further relates to a method of manufacturing an ulvan lyase by genetic recombination using a nucleic acid of the present invention or a vector of the present invention.

In some aspects of the present invention, a method of degrading ulvans comprises a step of bringing the ulvans into contact with an ulvan lyase of the present invention or with a host cell of the present invention or with a microorganism of the present invention, in conditions permitting degradation of the ulvans by enzymatic digestion by said protein or said host or said microorganism.

BRIEF DESCRIPTION OF THE DRAWINGS

FIG. 1 is a gel from electrophoresis of the ulvanolytic proteins of 30 kD (Gel A) and of 46 kD (Gel B) of the present invention. The arrows indicate the bands that were excised and then used for sequencing the peptides by mass spectrometry.

FIG. 2 shows the protein sequence of ulvan lyase of 46 Dka (SEQ ID No. 4) of the present invention with, in bold, the signal peptide or sequence (SEQ ID No. 3). In normal text, the catalytic module, determined by mass spectrometry, SEQ ID No. 1. The non-catalytic part of the protein sequence (SEQ ID No. 2) of the 46 kD protein is underlined.

FIG. 3 shows the sequence of the gene coding for the ulvan lyase protein of 46 Dka. In bold, the gene coding for the signal peptide or sequence (SEQ ID No. 7). In normal text, the gene SEQ ID No. 5 coding for the catalytic module of SEQ ID No. 1, determined by mass spectrometry. Underlined, the sequence SEQ ID No. 6 coding for the non-catalytic part of the 46 kD protein (SEQ ID No. 2) present in the 46 kD peptide.

DETAILED DESCRIPTION OF THE INVENTION

Figure 4:
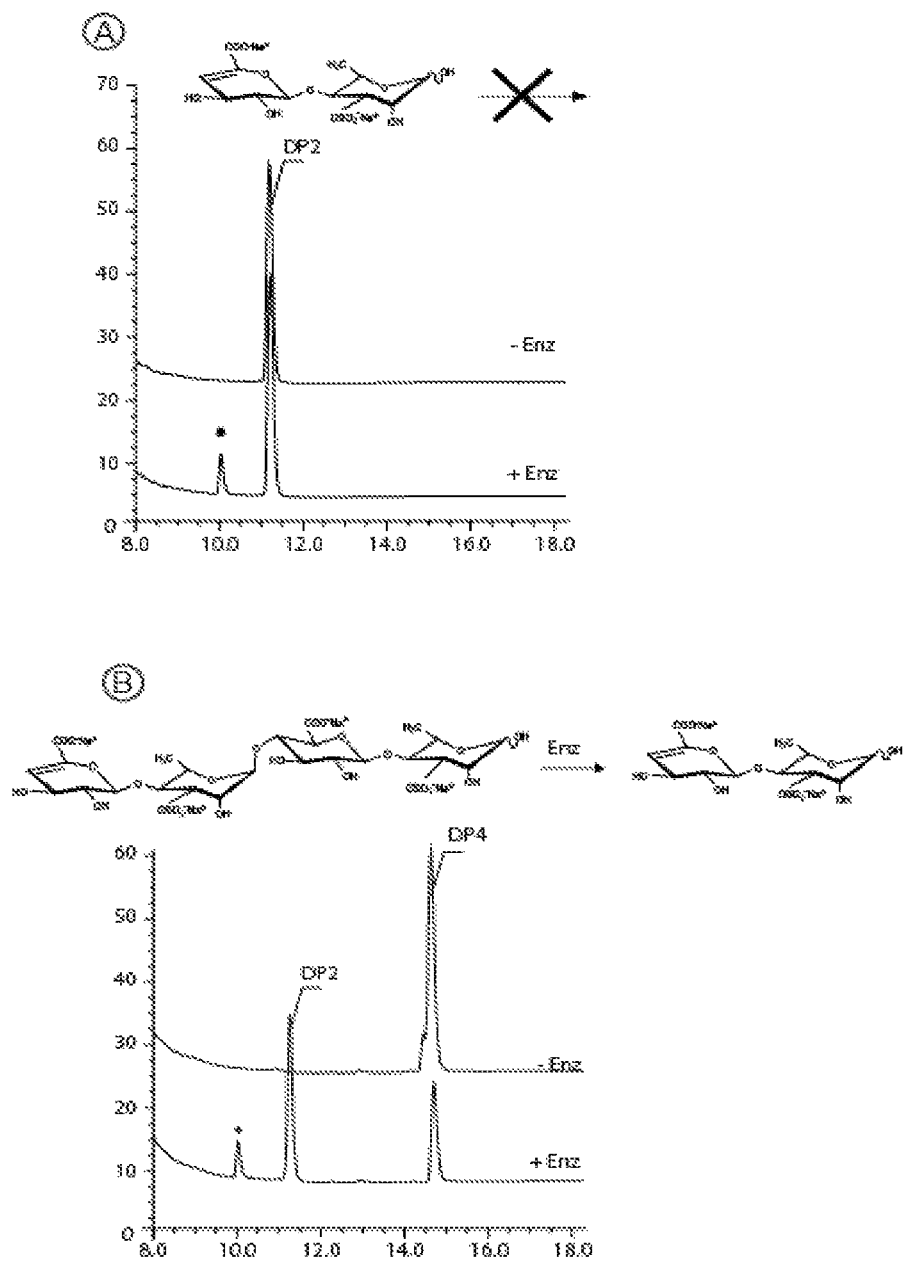
FIG. 4 shows the results obtained in ion exchange chromatography experiments conducted before or after incubation of a disaccharide (graph A) or of a tetrasaccharide (graph B) with the ulvan lyase of the present invention. On these graphs, the abscissa shows the elution time in minutes (min), and the ordinate shows the conductimetry in nano-coulomb (nC).

The aim of the present invention is precisely to meet this need by supplying ulvan lyases that degrade ulvans very effectively by depolymerization. Investigation of the conditions for recognition of the enzymes of the present invention undertaken by the inventors demonstrates their glucuronic lyase activity.

The inventors have also demonstrated iduronic and glucuronic lyase activity.

The inventors supply, in particular, ulvan lyases extracted from the microorganism deposited under number I-4324 in the National Collection of Cultures of Microorganisms (CNCM) 25 rue du docteur Roux, 75724 Paris Cedex 15, France. This microorganism is also called "01-PN-2010" in the present text and in the CNCM deposition documents.

In other words, the inventors supply, in particular, ulvan lyases extracted from the microorganism of marine origin deposited under number I-4324 in the National Collection of Cultures of Microorganisms (CNCM) 25 rue du docteur Roux, 75724 Paris Cedex 15, France.

These ulvan lyases, also called ulvanolytic proteins, can be for example of 30 or 46 kD and can comprise the following four sequences in their peptide sequence:

```
                                              (SEQ ID No. 9)
    PNDPNLK, (SEQ ID No. 10)
    LLEVGNTGTFGSTGS, (SEQ ID No. 11)
    DLANPDNV,
    and (SEQ ID No. 12)
    WNLPE.
```

The inventors have in fact notably isolated ulvan lyases of 30 kD or 46 kD having these sequences in common in their respective sequence. Although these proteins possess peptide fragments in common, their sequences have never been described in the prior art. These sequences of 30 or 46 kD are active for degrading the ulvans by depolymerization according to the present invention. They were extracted as indicated in the examples given below.

One of these sequences is the sequence SEQ ID No. 1 of 30 kD. The present invention therefore also relates to this sequence. This sequence is the catalytic moiety of an ulvan lyase isolated by the inventors and of 46 kD (SEQ ID No. 4). This ulvan lyase is shown in the accompanying FIG. 2.

The sequence ID No. 1 can therefore comprise, at its C-terminal end, the sequence SEQ ID No. 2 in the appended sequence listing.

According to the invention, these ulvan lyases, whatever their sequence, can further comprise, at their N-terminal end, a signal sequence or address sequence. This signal sequence can be one of the signal sequences known by a person skilled in the art so that the protein, when it is synthesized in a host cell, is directed to an organelle or a particular region of the host cell. It can be for example a signal sequence found in sites specializing in the prediction of signal peptides, for example the SignalP Server website [2] or the SIG-Pred: Signal Peptide Prediction website [3]. It can be for example the sequence SEQ ID No.3 in the appended sequence listing. This signal sequence can be cleaved after synthesis of the protein or otherwise. The methods of cleavage known by a person skilled in the art can be used, for example those involving proteases specific to a cleavage site. A signal sequence having such a site is then selected.

The present invention also relates to nucleic acids coding for the ulvan lyases of the present invention, notably for the protein SEQ ID No. 1. It can be for example a nucleic acid comprising or consisting of the sequence SEQ ID No. 5 in the appended sequence listing.

The present invention also relates to a nucleic acid coding for the protein of sequence SEQ ID No. 2 in the appended sequence listing. It can be for example the sequence SEQ ID No. 6 in the appended sequence listing.

The present invention also relates to a nucleic acid coding for the protein of sequence SEQ ID No. 3 in the appended sequence listing. It can be for example the sequence SEQ ID No. 7 in the appended sequence listing.

The present invention also relates to a nucleic acid coding for the protein of sequence SEQ ID No. 4 in the appended sequence listing. It can be for example the sequence SEQ ID No. 8 in the appended sequence listing.

These nucleic acid sequences or genes of the present invention are the first representatives of a new family of genes coding for polysaccharide lyases and also represent the first genes of enzymes according to the present invention for degradation of ulvan.

The present invention also relates to a vector comprising a nucleic acid coding for one of the ulvan lyases of the present invention, for example a nucleic acid selected from the sequences SEQ ID No.5 or 8. The vector can be one of the vectors known by a person skilled in the art for manufacturing proteins by genetic recombination. In general it is selected notably as a function of the cellular host selected. The vector can be for example selected from the vectors listed in the Promega catalogue [4] or the Qiagen catalogue [5], or the santa crus biotechnology, inc. catalogue [6]. It can be for example the expression vector described in the document WO 83/004261 [7].

The nucleic acids of the present invention or the vectors of the present invention are usable notably for manufacturing the ulvan lyases of the present invention by genetic recombination. Thus, the present invention also relates to a host cell comprising a nucleic acid sequence according to the invention or a vector according to the invention.

The host cell or cellular host can be any suitable host for manufacturing the ulvan lyases of the present invention from the nucleic acids or the vectors of the invention. It can be for example *E. coli, Pischia pastoris, Saccharomyces cerevisiae,* insect cells, for example an insect cells-baculovirus system (for example insect cells SF9 using a baculovirus expression system), mammals.

Thus, the present invention also relates to a method of manufacturing an ulvan lyase according to the invention by genetic recombination using a nucleic acid or a vector according to the invention. The methods of genetic recombination known by a person skilled in the art can be used. The marine or terrestrial origin has no influence on the possibility of recombination and of heterologous expression.

The present inventors are moreover the very first to have isolated a microorganism, which they named 01-PN-2010, which produces the ulvan lyases of the present invention. It is a marine bacterium. This marine bacterium is found for example in the faeces of *Aplysia punctata* (Mullusca, Gastropoda). They deposited this bacterium in accordance with the Budapest Treaty on the international recognition of the deposition of microorganisms for the purposes of patent procedure in the National Collection of Cultures of Microorganisms (CNCM) 25 rue du docteur Roux, 75724 Paris Cedex 15, France. The deposition number of this strain in the CNCM is I-4324.

The inventors purified, from this microorganism, the two ulvan lyases of 30 kD and 46 kD described in the present text.

Thus, the present invention also relates to the microorganism deposited under number I-4324 in the National Collection of Cultures of Microorganisms (CNCM) 25 rue du docteur Roux, 75724 Paris Cedex 15, France.

This microorganism can therefore be used notably for manufacturing ulvan lyases. The present invention therefore also relates to a method of manufacturing ulvan lyases comprising culturing the microorganism deposited under number I-4324 in the CNCM in France.

This culturing is preferably carried out in a culture medium permitting the growth of this marine microorganism. It can be for example ZoBell liquid culture medium, as described in the document ZoBell, CE 1941 Studies on marine bacteria. I. The cultural requirements of heterotrophic aerobes, J Mar Res 4, 41-75 [8]. Culture conditions usable for implementing the present invention are also described in this document. The culture pH is preferably between 7 and 9, preferably pH 8. The culture temperature is preferably between 15 and 30° C., preferably 25° C. Culture is preferably carried out with an NaCl concentration from 20 to 30 g·L$^{-1}$, preferably 25 g·L$^{-1}$.

This method of manufacturing ulvan lyases using the microorganism of the invention or any other host cell transformed for manufacture by genetic recombination according to the present invention, can further comprise a step of recovery of the ulvan lyases. This step of recovery or of isolation can be carried out by any means known by a person skilled in the art. It can be for example a technique selected from electrophoresis, molecular sieving, ultracentrifugation, differential precipitation, for example with ammonium sulphate, by ultrafiltration, membrane filtration or gel filtration, ion exchange, elution on hydroxyapatite, separation by hydrophobic interactions, or any other known means. An example of a method of isolating these ulvan lyases usable for carrying out the present invention is described below.

The aforementioned microorganism or any other host cell transformed for manufacture by genetic recombination according to the present invention can also be used directly for degrading ulvans, in their natural environment or in culture. When it is a culture, it can be a batch system or a continuous system. For example, a culture reactor can be used containing a culture medium suitable for the development of the microorganism.

The present invention therefore also relates to a method of degrading ulvans comprising a step of bringing the ulvans into contact with an ulvan lyase according to the invention or with a host cell according to the invention or with the microorganism deposited under number I-4324 in the CNCM in France, in conditions permitting degradation of the ulvans by enzymatic digestion by said ulvan lyase or said transformed host cell or said microorganism deposited under number I-4324 in the CNCM in France.

The conditions permitting degradation of the ulvans, when a host cell or microorganism is used, are those presented above, for the host cell or for the microorganism, respectively.

For enzymatic digestion, determination of the Michaelis Menten constants (Km and Vmax) easily enables a person skilled in the art to find optimum concentration conditions of the ulvan lyase used and concentration of the ulvans for degradation of the ulvans in the environment where they are located or in the medium in which they have been placed. The pH can also preferably be between 7 and 8, preferably between 9 and 9.5. It is in fact the optimum pH range. The (optimum) temperature is preferably between 30° C. and 40° C. The strength. The ionic strength above 300 mM NaCl for the protein of 46 kD and without salt with the protein of 30 kD, in another embodiment, the optimum ionic strength is 300 mM NaCl for the protein of 46 kD and 100 mM NaCl for the protein of 30 kD.

The invention advantageously allows mobilization of the very large resource of algae that is currently unexploited, notably of green algae. The invention makes it possible, moreover, to promote the biodegradation of the algae, notably of the green algae, to produce original molecules, which are fragments of ulvans or oligo-ulvans, for example oligosaccharides, for example also hydrocolloids, and to offer a new source of rare monosaccharides for cosmetic and food-processing applications, medicinal products or pharmaceutical and parapharmaceutical formulations.

The products of degradation of the ulvans give access to new products, which may be food-processing, cosmetic, pharmaceutical and parapharmaceutical active substances usable in the food-processing, cosmetic, pharmaceutical and parapharmaceutical fields. These new products may also be products that are not active, but display a neutrality and/or a stability that is very interesting for use in each of these fields.

The use of the ulvan lyases of the present invention moreover gives access to rare monosaccharides usable as synthons in glycochemistry. The degradation of ulvan with ulvan lyases combined with other enzymes can give access to iduronic acid (a rare sugar) used for the synthesis of synthetic glycoaminoglycans.

The present invention also opens up new perspectives for the use of these algae for applications in bioenergy and in chemistry. The production of oligosaccharide fragments can give base molecules for manufacturing other molecules. The depolymerization of ulvan should facilitate fermentation by microorganisms leading to the production of methane for example.

Other features and advantages will become clearer to a person skilled in the art on reading the following examples, given for purposes of illustration and non-limiting, referring to the appended drawings.

EXAMPLES

Example 1

Identification of the Microorganism of the Present Invention

Several individuals of *Aplysia punctata* (Mollusca, Gastropoda) were fed with green algae belonging to the genus *Ulva* (*Ulva* sp.), in particular *Ulva armoricana*. The faeces of the molluscs were collected and then frozen for storage at −80° C.

A fraction of the faeces was collected and served as inoculum in a POPSO culture medium. In particular, this fraction of faeces was incubated with stirring, rotation at 200 rpm, in an incubator that controls temperature and rotation at 20° C. for 72 hours in 5 mL of POPSO culture medium (piperazine-N, N'-bis[2-hydroxypropane-3-sulphonic] acid), which has the following composition:
25 mM of POPSO buffer pH 7.0,
50 mM NaCl,
0.4 g of casamino acid,
3 g of ulvan,
1 L of seawater.

The ulvan used here and in the examples given below was prepared by the method described in the document Lahaye M. et al., Method of extraction of ulvans, (1996) Hydrobiologia, 326/327, 473 [9].

Another fraction of the faeces was incubated with stirring for 72 h in 5 mL of ZoBell 2216E culture medium (ZoBell, 1941) (see ZoBell et al. [8]). The ZoBell medium used comprises the following elements (for 1 L of ZoBell medium): 5 g of bactotryptone, 1 g of yeast extract, 200 mL of distilled water and 800 mL of seawater.

Each of the liquid cultures was then spread on agar dishes containing ZoBell culture medium enriched with ulvan or "agar-ZoBell-ulvan dishes". These solidified ZoBell media comprised, besides the above composition, 1.5 wt % of agar (15 g) and 0.4 wt % of ulvan. The ZoBell-agar dishes were maintained at 20° C. for one week.

After culture for one week at 37° C., colonies appeared possessing very different phenotypic characteristics (colour, size, shape, etc.). These colonies were isolated and subcultured several times on agar-ZoBell-ulvan dishes, each time with culture for a time enabling the colonies to be seen at a temperature of 20° C. About twenty strains were isolated.

All the strains isolated were cultured for 24 hours at 20° C. in ZoBell liquid culture medium enriched with 0.4 wt % of ulvan. After centrifugation at 1000×g, the bacterial pellets were lysed using a French press or with a chemical lysis buffer and then centrifuged at 1000×g.

The supernatants of bacterial cultures and the supernatants of the bacterial lysates were examined separately after being incubated in the presence of ulvan. For this, 50 µL of bacterial culture supernatant or 5 µL of bacterial lysate was added each time to 1 mL of reaction mixture comprising, in wt %: 1% of ulvan, 200 mM NaCl in 20 mM Tris-HCl, pH 7.7.

The double bond formation produced by the activities of the ulvan lyases optionally present in the extracts was monitored by spectrophotometry at 235 nm and the depolymerization of the polysaccharide was observed by electrophoresis (C-PAGE) and by gel filtration chromatography.

Four of the twenty strains isolated had a very strong ulvanolytic activity in the bacterial lysates and the culture supernatants.

The most active strain was referenced under the name 01-PN-2010 and was then used for purification of the ulvan lyases (examples 2 and 3). This strain was deposited in the National Collection of Cultures of Microorganisms (CNCM) 25 rue du docteur Roux, 75724 Paris Cedex 15, France, under number I-4324.

Example 2

Finding the Optimum Conditions for Culture of Strain 01-PN-2010 of the Present Invention and Characterization of the Strain Various cultures of strain 01-PN-2010 were carried out in a ZoBell 2216E medium, as in example 1, at temperatures of 4, 10, 20, 30, 37 and 42° C. for 24 h. The growth of 01-PN-2010 was observed by measuring the optical density at 600 nm, using a Shimadzu (trademark) spectrophotometer. Growth is observed from about 4° C. to 35° C., growth is optimum between 20 and 30, and especially around 25° C.

The optimum culture pH was determined at 20° C. on ZoBell medium, adding various buffers:
  20 mM of MES buffer for pH 5.5, 6 and 6.5;
  20 mM of MOPS buffer for pH 7;
  20 mM of HEPES buffer for pH 7.5
  20 mM of TRIS-HCl buffer for pH 8 and 8.5;
  20 mM CHES buffer for pH 9, 9.5 and 10.

Growth of 01-PN-2010 was observed between pH 6.5 and 9 after incubation for 3 days, with optimum growth at pH 7.5 to 8.

The effect of NaCl on growth was also tested on ZoBell medium, at 20° C. and pH 8, with different concentrations of NaCl: 0, 0.25, 0.5, 1.0, 2.0, 3.0, 4.0, 5.0, 6.0, 8.0, 10, 25, 30, 40, 50, 55, 60, 65, 70 and 80 g·l$^{-1}$. After incubation for 2 days, growth was observed in ZoBell media comprising 2.0 to 65 g·l$^{-1}$ of NaCl, with an optimum at around 25 g·l$^{-1}$ (2.5% w/v).

In the following optimum conditions identified:
  culture temperature from 15 to 30° C., preferably 15 to 25° C., preferably 25° C.;
  pH between 7 and 10, between 7 and 9, preferably pH 8;
  20 to 30 g·L$^{-1}$ of NaCl, preferably 25 g·L$^{-1}$ of NaCl,
the doubling time of the strain is 3 hours.

The colonies on a ZoBell 2216E Agar medium in a Petri dish are circular, shiny, orange, with a diameter of 2 to 3 mm after incubation for 5 days at 20° C. Culturing the strain on ZoBell-ulvan medium in a Petri dish for 24 hours at 20° C. causes formation of a hole, which results from hydrolysis of the ulvan by the strain.

Example 3

Purification of an Ulvan Lyase According to the Invention of 30 kD

The purification was carried out starting from a culture of 1 L of ZoBell medium (see above for composition) with 0.4 wt % of ulvan inoculated with 50 mL of a fresh culture of 01-PN-2010 possessing an optical density at 600 nm.

The culture was conducted in a conical flask and maintained at 20° C. for 96 hours with stirring at 230 rpm (apparatus, see above). Throughout bacterial growth, the ulvanolytic activity was monitored by spectrometry at 235 nm.

The bacteria were removed from the culture medium by centrifugation at 7500×g, for 30 min at 10° C. The supernatant was concentrated to 120 mL by tangential flow ultrafiltration on a 10-kD filter (Prep/Scale (trademark)-TFF, Milipore).

A fraction of the proteins was precipitated by adding 1M $(NH_4)_2SO_4$ in small amounts with gentle stirring of the solution, maintained in ice.

The precipitate was removed after centrifugation at 20 000×g at 10° C. and the supernatant possessing ulvanolytic activity was used for the rest of the purification.

The whole supernatant was injected on a HiTrap phenyl-sepharose high sub column (1 mL; GE Healthcare) equilibrated with buffer A [20 mM Tris-HCl pH 7.5, 1M $(NH_4)_2SO_4$] at a flow rate of 1 mL min$^{-1}$ at room temperature, here 22° C. The gel was washed with 2 column volumes of buffer A.

Elution of the proteins was performed by applying a linear gradient decreasing from 1 M to 0 M $(NH_4)_2SO_4$ [buffer A without $(NH_4)_2SO_4$ respectively] on 20 column volumes.

The active fractions (15 mL) were combined and then desalted on a HiPrep desalting column (2.6×30 cm; GE Healthcare) equilibrated in buffer B [20 mM Tris-HCL, pH 8.0]. The flow rate for loading and elution was 3 mL min$^{-1}$.

The desalted sample was loaded on a HiTrap Q FF column (1 mL; GE Healthcare) equilibrated with buffer B. The gel was washed with 2 column volumes of buffer B before elution with a linear gradient of NaCl in buffer B from 0 M to 1 M on 20 column volumes.

The active fractions were combined and loaded on a HiTrap heparin HP column (1 mL; GE Healthcare) equilibrated with buffer C [phosphate buffer 10 mM, pH 7.0] at a flow rate of 1 mL min$^{-1}$.

The gel was washed with 2 column volumes of buffer C before elution with a linear gradient of NaCl in buffer C from 0 M to 1 M on 20 column volumes.

The active fractions (5 mL) were combined and loaded on a column of Superdex 75 HiPrep (1.6×60 cm; GE Healthcare) equilibrated with buffer B with 100 mM NaCl.

The proteins were eluted with an isocratic gradient with the same buffer at 1 mL min$^{-1}$.

The inventors thus isolated a protein of 30 kD. This protein is an active ulvan lyase. They observed slight contamination with two other less abundant proteins of very similar molecular weights.

The main 30 kD protein was digested with trypsin, then the peptides obtained were analysed by mass spectrometry on the R10 "Biopolymers" platform located at the NRA in Nantes. The results of analysis and of sequencing are presented in Table 1 of example 5 below.

Example 4

Purification of Another Ulvan Lyase According to the Invention

The purification of this other ulvan lyase was performed starting from a culture of 01-PN-2010 in a 5-L fermenter in the ZoBell medium described above with 0.4 wt % of ulvan, at 25° C. and with a pH maintained at pH 7.8 for 48 hours.

The bacteria were removed by centrifugation at 8000 g, for 1 h at 10° C. The supernatant was concentrated to 220 mL by tangential ultrafiltration on the millipore system (Prep/Scale (trademark)-TFF) with a 10-kD filter. As before, the proteins were precipitated by adding 1 M $(NH_4)_2SO_4$.

The pellet was removed after centrifugation at 20 000 g, for 30 min at 10° C.

30 mL of 6 high sub phenylsepharose resin equilibrated with buffer B with 1M $(NH_4)_2SO_4$ was added to the supernatant and stirred gently for 30 min. The resin was separated from the medium by filtration on a glass frit. The resin was then washed with two volumes of 75 mL of buffer B with 1 M $(NH_4)_2SO_4$ and elution was carried out with buffer B in 25-mL aliquots on a glass frit.

The rest of the purification was carried out in the same way as for the 30 kD protein in the preceding example. The active fractions (100 mL) were loaded on a HiTrap phenyl-sepharose high sub column (1 mL; GE Healthcare) equilibrated in buffer B with 1 M $(NH_4)_2SO_4$ at a flow rate of 1 mL $min^{-1}$ at room temperature, here 22 or 20° C.

The active fractions (30 mL) were mixed and desalted on a HiPrep desalting column (2.6×30 cm; GE Healthcare) equilibrated in buffer D [20 mM Bis-Tris pH 6.0].

The desalted sample was loaded on a HiTrap DEAE column (1 mL; GE Healthcare) equilibrated with buffer D at 1 mL $min^{-1}$. The gel was washed with 5 column volumes of buffer D before elution with a linear gradient of NaCl of up to 1 M in buffer D.

The active fractions were mixed (7 mL) and diluted to 50 mL in buffer B before loading on a HiTrap Q FF column (1 mL; GE Healthcare) equilibrated with buffer B. The gel was washed with 5 column volumes of buffer B before elution with a linear gradient of NaCl of up to 1 M in buffer B.

The active fractions (5 mL) were put and injected together on a Superdex 75 HiPrep column (1.6×60 cm; GE Healthcare) equilibrated with buffer B with 100 mM NaCl.

The proteins were eluted with an isocratic gradient with the same buffer at 1 mL $min^{-1}$.

The active fractions (15 mL) were mixed and dialysed overnight against buffer C.

The desalted sample was loaded on a HiTrap heparin HP prepacked column (1 mL; GE Healthcare) equilibrated with buffer C [10 mM phosphate buffer pH 7.0] at a flow rate of 0.5 mL $min^{-1}$. The gel was washed with 2 column volumes of buffer C before elution with a linear gradient of NaCl in buffer C from 0 M to 1 M on 20 column volumes.

At each step of the purification, the active fractions were analysed by SDS-PAGE according to the technique described in the document LaemmLi UK and Favre M 1973 Links maturation of the head of bacteriophage T4.I. DNA packaging events. J Mol Biol 80: 575-599 [10].

Protein quantitation was performed according to the technique described in the document Bradford M M 1976; A rapid and sensitive method for the quantitation of microgram quantities of protein using the principle of protein-dye binding. Anal Biochem 72: 248-254 [11] using the Biorad reagent [Biorad protein assay (trademark)] with bovine serum albumin as standard.

The activity of the ulvan lyase extracted was analysed by a spectrophotometric method: 25-50 μL of extract is added to 1 mL of reaction mixture [20 mM Tris-HCL pH 7 or 8.5, 200 mM NaCl and 1 wt % of ulvan]. The increase in absorbance at 235 nanometers was monitored for 5 min.

For identification of the active fractions, the inventors used a method of detection in a Petri dish according to the method described in the document Gacesa P and Wusteman F S 1990 Plate assay for simultaneous detection of alginate lyases and determination of substrate specificity. Appl and Environ Microbiol 56: 2265-2267 [12].

Two-microliter aliquots of the protein fractions are deposited on agarose gels (1 wt % of agarose, 0.1 wt % of ulvans, 20 mM Tris-pH 7.7 or 8.5, 200 mM NaCl). The Petri dish was kept overnight at room temperature, here 20° C., and the presence of enzymatic activity is detected by adding a solution of ruthenium red (0.5 wt % in water) for 10 minutes or for 10-to 30 minutes. The active fractions are identified by light (unstained) patches on a pink background.

The purified proteins migrated on electrophoresis gel and were then stained with colloidal blue. The protein bands were excised from the SDS-PAGE gels and were analysed by mass spectrometry on the RIO "Biopolymers" platform, INRA, in Nantes.

The inventors thus isolated a protein of 46 kD of sequence SEQ ID No. 4.

The sequences of the peptides obtained after incubation with trypsin had no significant homology with sequences of the prior art in the TrEMBL database despite the large size of the peptide fragments sequenced.

The proteins, called ulvanolytic proteins, of 30 kD isolated in example 3 and of 46 kD isolated in the present example were purified on electrophoresis gel as shown in the accompanying FIG. 1: electrophoresis gel of the 30 kD protein (Gel A) and of the 46 kD protein (Gel B). The arrows indicate the bands that were excised and then used for sequencing the peptides by mass spectrometry.

TABLE 1

Peptide sequences obtained from ulvanolytic proteins of 30 kD and 46 kD by sequencing de novo Molecular weight

| 30 kD | | 46 kD | |
|---|---|---|---|
| Sequences | SEQ ID NO. | Sequences | SEQ ID NO. |
| PNDPNLK | 9 | PNDPNLK | 9 |
| BLLEVGNTGTFGSTGSA | 13 | LLEVGNTGTFGSTGSYLMQAK | 30 |
| DLANPDNV | 11 | DLANPDNVGTVDDR | 31 |
| ALLGGQVFNWNLPES | 14 | QEMALLMQEVDWNLPE | 32 |
| BEQLNFR | 15 | ---------ADLYR | 33 |
| LELLDLELE | 16 | VVDNSTLPAADLYR | 34 |
| TGVGSYAR | 17 | ADLYR | 35 |
| BPVYG-NQVQVSFDLWR | 18 | YHDTNNMLTHSANLDDR | 36 |
| GGGGSNDPALCLYLAR | 19 | LYENGELVDEFL | 37 |
| ACPSSGVFQ | 20 | | |
| LLSGWG | 21 | | |
| BVYDNTLV | 22 | | |
| FGVTGPPT | 23 | | |
| DLLGNTLD | 24 | | |

TABLE 1-continued

Peptide sequences obtained from ulvanolytic proteins of 30 kD and 46 kD by sequencing de novo Molecular weight

| 30 kD | | 46 kD | |
|---|---|---|---|
| Sequences | SEQ ID NO. | Sequences | SEQ ID NO. |
| | | BDTDLPNPR | 25 |
| | | ATGAG | 26 |
| | | BSCYANYSESSLLGK | 27 |
| | | BDDPNNP<u>GQTLHYAW</u>K | 28 |
| | | B<u>FWGLYNLTD</u> | 29 |

The sequences in bold correspond to the sequences common to the ulvan lyases of 30 and 46 kD of the present invention. The first four peptides are common to both proteins. These data, when compared with the TrEMBL database, did not allow a homologous sequence comprising these four sequences to be identified in a single protein.

The sequences underlined were used for constructing the degenerate primers used in the next example.

Example 5

Identification of a Coding Gene 5.1) Degenerate Primers

Six degenerate primers were synthesized based on the peptide sequences common to the proteins of 30 and 46 kD obtained from mass spectrometry in both directions (Forward: F and Reverse: R; Table 2).

PCR amplification was performed with all the possible combinations of the primers on 75 ng of genomic DNA of 01-PN-2010 in 25 µL of reaction mixtures containing GoTaq PCR 1× buffer, 1 mM MgCl$_2$, 0.2 mM of each dNTP, 2 µM of the Forward and Reverse primers, and 1.25 U GoTaq (Promega). The amplification programme was 94° C. for 2 minutes, thirty-five cycles of: 94° C. for 30 s, 50° C. for 30 s and 72° C. for 1 min 30 s followed by a final step at 72° C. for 7 minutes. Then the samples were maintained at 4° C. before sequencing.

In this way the inventors obtained a 700 bp fragment of the ulvan lyase gene.

5.2) "TAIL-PCR"

The TAIL-PCR method described in the document Liu Y G and Whittier R F 1995 Thermal Asymmetric Interlaced PCR: Automatable Amplification and Sequencing of Insert End Fragments from P1 and YAC Clones for Chromosome walking. Genomics 25: 674-681 [13] was used for obtaining the sequence of the ends of the ulvan lyase gene.

The "specific" primers are degenerate primers designed on the basis of the sequence fragments of the known gene (Table 2). Five different "arbitrary" degenerate primers were selected from those determined in the literature (Table 2 in the document Liu and Whittier et al. [6], and in the document Liu Y G, Mitsukawa N, Oosumi T and Whittier R F 1995 Efficient isolation and mapping of *Arabidopsis thaliana* T-DNA insert junctions by thermal asymmetric interlaced PCR. Plant J. 8: 457-463 [14]).

The amplification programmes were different for the different reactions of TAIL-PCR (Table 3) and are based on the programmes of Liu et al., 1995 [14] but adapted to the PCR machines available to the laboratory.

TABLE 2

Primers used for identifying the ulvan lyase gene (F: forward, R: reverse)

| Primer | SEQ ID NO. | Sequence (5' to 3') | SEQ ID NO. | T$_m$ |
|---|---|---|---|---|
| *Degenerate primers of ulvan lyase* | | | | |
| VGNTGTFG-F | 64 | GTN GGN AAY ACN GGN ACN TTY GG | 38 | 52-64 |
| PNDPNLK-F | 9 | CCN AAY GAY CCN AAY YTN AA | 39 | 42-56 |
| ANPDNVG-F | 65 | GCN AAY CCN GAY AAY GTN GG | 40 | 48-60 |
| TLPAADLY-F | 66 | ACN YTN CCN GCN GCN GAY YTN TA | 41 | 50-66 |
| GGQVFNW-F | 67 | GGN GGN CAR GTN TTY AAY TGG | 42 | 49-60 |
| GQTLHYAW-F | 68 | GGN CAR ACN YTN CAY TAY GCN TGG | 43 | 52-66 |
| VGNTGTFG-R | 64 | CCR AAN GTN CCN GTR TTN CCN AC | 44 | 52-64 |
| PNDPNLK-R | 9 | TTN ARR TTN GGR TCR TTN GG | 45 | 42-56 |
| ANPDNVG-R | 65 | CCN ACR TTR TCN GGR TTN GC | 46 | 48-60 |
| TLPAADLY-R | 66 | TAN ARR TCN GCN GCN GGN ARN GT | 47 | 50-66 |
| GGQVFNW-R | 67 | CCA RTT RAA NAC YTG NCC NCC | 48 | 49-60 |
| GQTLHYAW-R | 68 | CCA NGC RTA RTG NAR NGT YTG NCC | 49 | 52-66 |
| *Specific primers for TAIL-PCR* | | | | |
| UL_133R | — | CTAG GTT GTA ATG TGT TAG GTG CAT CCC | 50 | 60 |
| UL_194R | — | GTG AAT CGC GCA TAA CTT CCC ACA CC | 51 | 61 |
| UL_285R | — | CC CGT GTG CTT ACC TTT GGC CTG C | 52 | 63 |
| UL_426F | — | GC AGC TGG AAG AAC CGA GGT CTT TC | 53 | 61 |
| UL_582F | — | CCG GAA CCA GAA CGA GGA AGA GAA TC | 54 | 61 |
| UL_643F | — | GGA GGA AGA GCA CAA ATG AGA TGG GC | 55 | 61 |
| AfterUL 1F | — | CAC GTA ATC TGG GTA GGT TTT TAT ATC ATG ATA CC | 56 | 61 |
| AfterUL 2F | — | GCT TCT GTA GGT GTG TAT CCT AAC CC | 57 | 60 |
| AfterUL 3F | — | GCT GGA CGT GTG TCT TCT TTG TAT TAC GC | 58 | 62 |

TABLE 2-continued

Primers used for identifying the ulvan lyase gene (F: forward, R: reverse)

| Primer | SEQ ID NO. | Sequence (5' to 3') | SEQ ID NO. | $T_m$ |
|---|---|---|---|---|
| Arbitrary degenerate primers for TAIL-PCR | | | | |
| AD1 | — | TGW GNA GWA NCA SAG A | 59 | 38-43 |
| AD2 | — | AGW GNA GWA NCA WAG G | 60 | 38-43 |
| AD3 | — | WGT GNA GWA NCA NAG A | 61 | 38-43 |
| AD4 | — | NTC GAS TWT SGW GTT | 62 | 36-39 |
| AD5 | — | NGT CGA SWG ANA WGA A | 63 | 38-43 |
| Arbitrary primers for cloning in pFO4 | | | | |
| UL_BglII_F | — | GGG GGG AGA TCT GCG CCT GAT GAG GAT ACA AAT TCT | 69 | — |
| UL_EcoRI_R | — | CCC CCC CAA TTG TTA TCC TGA CGT ACT TGC GAT AAT GCT | 70 | — |

TABLE 3

Amplification conditions used for TAIL-PCR

| Reaction | Number of cycles | Temperatures and times |
|---|---|---|
| Primary | 1 | 93° C., 2 min |
|  | 5 | 94° C., 1 min; 62° C., 1 min; 72° C., 2 min |
|  | 2 | 94° C. 1 min; ramping to 25° C. over 3 min; 25° C., 3 min; ramping to 72° C. over 3 min; 72° C., 2 min |
|  | 15 | 94° C., 30 s; 65° C., 1 min; 72° C., 2 min; 94° C., 30 s; 65° C., 1 min; 72° C., 2 min; 94° C., 30 s; 45° C., 1 min; 72° C., 2 min |
|  | 1 | 72° C., 7 min; 4° C., ∞ |
| Secondary | 1 | 93° C., 1 min |
|  | 13 | 94° C., 30 s; 62° C., 1 min; 72° C., 2 min; 94° C., 30 s; 62° C., 1 min; 72° C., 2 min; 94° C., 30 s; 45° C., 1 min; 72° C., 2 min |
|  | 1 | 72° C., 7 min; 4° C., ∞ |
| Tertiary | 1 | 93° C., 1 min |
|  | 20 | 94° C., 30 s; 45° C., 1 min; 72° C., 2 min |
|  | 1 | 72° C., 7 min; 4° C., ∞ |

Example 6

Protocol for Digestion of Ulvans by the Ulvan Lyases of the Present Invention

25 µL of a fraction of pure ulvan lyase with a concentration of 5.7 µg protein per ml was added to 1 mL of reaction mixture composed of NaCl (200 mM), ulvan (1 g L-1) and Tris HCl (20 mM, pH 9.2) at 35° C. in a quartz cuvette. The degradation of the ulvan (or rather double bond formation) was monitored from the increase in absorbance at 235 nm.

Example 7

Degradation of Oligo-Ulvans by the Ulvan Lyases of the Present Invention

FIG. 4 shows the results obtained in ion exchange chromatography experiments conducted before or after incubation of a disaccharide (graph A) or of a tetrasaccharide (graph B) with the ulvan lyases of the present invention obtained in the above examples, in the same conditions as in the preceding example.

The degradation of the tetrasaccharide demonstrates the glucuronic lyase activity of the enzyme. On these graphs, the abscissa shows the elution time in minutes (min), and the ordinate shows conductometry in nano-coulomb (nC).

Example 8

Heterologous Expression and Degradation of Oligo-Ulvans by the Ulvan Lyases of the Present Invention The catalytic module of the ulvan lyase gene identified in the above example 5 was amplified with specific primers permitting incorporation of the BglII and EcoRI restriction sites at the 5' and 3' ends of the fragment, respectively (Table 2).

Standard PCR conditions, namely 1× GoTaq PCR buffer, 1 mM $MgCl_2$, 0.2 mM of each dNTP, 2 µM of the forward "sense" and reverse "anti-sense" primers, 1.25 U GoTaq (Promega) and 15 ng genomic DNA, were used with a hybridization temperature of 50° C. and 30 cycles of polymerization. The PCR products were then purified, digested by the appropriate restriction enzymes i.e. BglII and EcoRI and subcloned into the modified pFO4 expression vector of pET15 (Novagen) to be compatible with the BamHI/EcoRI and BglII/MfeI ligation strategies.

The recombinant plasmids were used for transforming the BL21 strain (DE3) of *Escherichia coli* prepared in the laboratory according to the protocol of Cohen, S N, Chang A C Y, Hsu L (1972) Nonchromosomal antibiotic resistance in bacteria: genetic transformation of *Escherichia coli* by R-factor DNA. Proc. Natl. Acad. Sci. USA 69: 2110-2114 [15]. Transformed colonies were cultured at first for 3 h at 37° C. in an expression medium based on Luria-Bertani (10 g tryptone, 5 g yeast extract and 10 g NaCl per L) with ampicillin and 0.5% glucose. Then an equal volume of cold Luria-Bertani medium with 0.6% lactose, 20 mM Hepes pH 7.0 and 1 mM of isopropyl β-D-1-thiogalactopyranoside (IPTG) was added and the culture was incubated at 20° C. for 18 h.

After centrifugation, the bacterial pellet was suspended in a buffer of 20 mM Tris-HCl, 500 mM NaCl and 5 mM imidazole with a pH of 7.4. Cell lysis was performed in a French press and the bacterial debris was removed by centrifugation at 20000 rpm. The supernatant was applied on a column of Ni Sepharose loaded with 100 mM $NiSO_4$ (GE Healthcare). After washing, the attached proteins were eluted with a linear gradient of imidazole from 5 mM to 500 mM. The active fractions were combined and desalted on a HiPrep 26/10 desalting column at equilibrium in 20 mM Tris-HCl pH 8.0.

The active fractions were identified by the Petri dish assay described in example 4.

Figure 5:
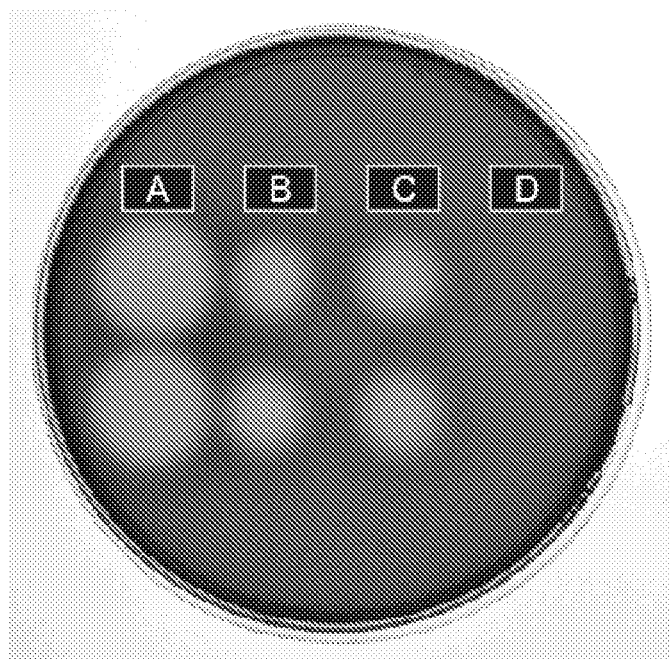
FIG. 5 is a photograph showing Petri dishes with ulvans labelled with an aqueous solution of ruthenium red at 0.05% showing the enzymatic degradation of the ulvans by the purified ulvan lyase of 30 kD (A), 46 kD (B) and the recombinant catalytic module (C). An extract comprising *E. coli* bacteria lacking an expression plasmid was also deposited on agar as control (D).

The heterologous expression of the catalytic module of ulvan lyase showed degradation of ulvans in the Petri dishes, light patches in FIG. 5, thus confirming the catalytic function.

2. High-Performance Anion Exchange Chromatography (HPAEC)

The purity of the fractions of oligosaccharides and the kinetics of degradation of pure oligosaccharides were analysed by HPAEC with a Dionex ICS 3000 chromatograph equipped with a 20 μL, injection loop, a type AS100XR automatic injection system (Thermo Separation Products) and an anion exchange column AS11 anion (4 mm×250 mm, Dionex IonPac) together with an AG11 guard column (4 mm×50 mm, Dionex IonPac). The system was operated in conductivity mode using an ED40 detector (Dionex) and a Dionex ASRS ultra-4 mm suppressor with a current of 300 mA. The mobile phases were ultrapurified water and 290 mM of NaOH. Elution was performed at a flow rate of 0.5 mL $min^{-1}$ with a GP40 gradient pump. The gradient used was 0 min, 3% B; 1.5 min 1% B; 4.1 min 5% B; 6.5 min 10% B; 10.0 min 18% B; 26 min 22% B; 28 min 40% B; 30 min 100% B; 30.1 min 3% B; 37 min 3% B. The Chromeleon-peak Net software program (Dionex) was used for data acquisition and transfer. The di- and tetrasaccharides were incubated with the purified ulvan lyases of the invention and analysed by HPAEC.

Figure 6:
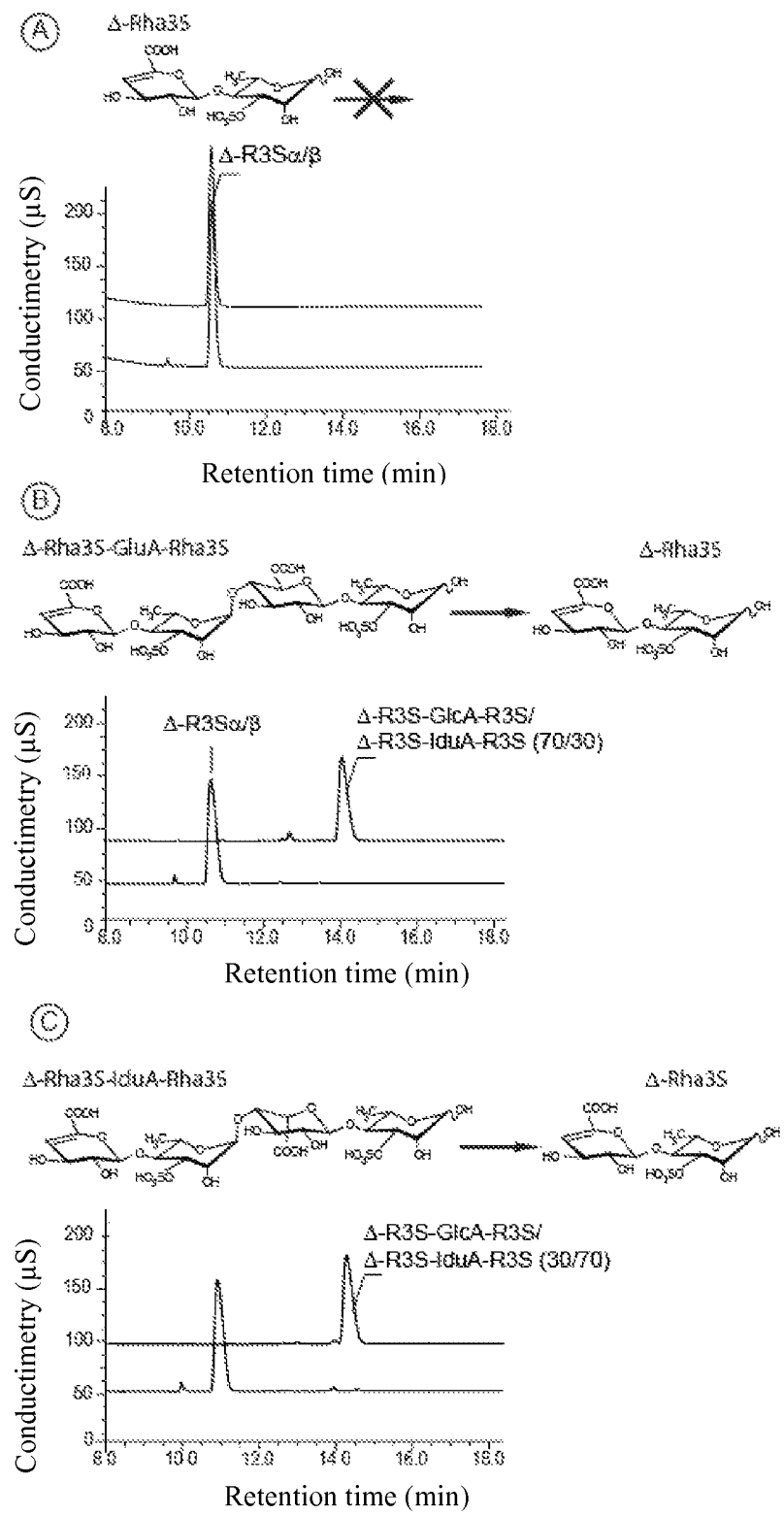
FIG. 6 shows the results obtained from experiments of high-performance anion exchange chromatography of purified oligosaccharides. (A) Δ-R3S has not been degraded by the ulvan lyase. (B) The tetrasaccharide Δ-R3S-Glc-R3S was converted solely to Δ-R3S after incubation with the ulvan lyase. (C) The tetrasaccharide Δ-R3S-Idu-R3S was converted solely to Δ-R3S after incubation with the ulvan lyase, as also observed in (B). On these graphs, the abscissa shows the elution time in minutes (min), and the ordinate shows the conductometry in microsiemens (μS).

The Δ-R3S disaccharide, i.e. (4-deoxy-L-threo-hex-4-enopyranosiduronic acid bound at 4 to L-Rhap 3-sulphate) FIG. 6 A and the tetrasaccharide Δ-R3S-Xyl-R3S were not changed by the enzymes and are final products. The mixture of Δ-R3S-GlcA-R3S and Δ-R3S-IduA-R3S tetrasaccharides (70:30, 50:50 and 30:70, GlcA:IduA ratios) were converted completely to a single disaccharide: Δ-R3S, showing that the ulvan lyase had cleaved the glycosidic bond between the sulphated rhamnose and either the glucuronic or iduronic residue. FIGS. 6 B and C present the results obtained, showing the peaks of each saccharide. The kinetics of degradation of these mixtures was monitored by HPAEC to highlight the possible differences in recognition of the glucuronic or iduronic residues.

However, the rate of degradation of the mixtures of tetrasaccharides and the rate of production of the disaccharide Δ-R3S were independent of the ratio GlcA:IduA. The rates of degradation of 0.18±0.05 μM/min and 0.08±0.02 were observed for the ulvan lyases of 30 kD and 46 kD. The degradations were performed with concentrations of tetrasaccharides 1.5 mM in 200 mM of ammonium carbonate at 30° C.

As demonstrated in this example, the ulvan lyases of the invention therefore permit cleavage at the level of glucuronic acid as well as at the level of iduronic acid, demonstrating that the ulvan lyase of the present invention has an activity that is different and greater than those of the prior art.

LIST OF REFERENCES

[1] Marc Lahaye and Audrey Robic, Structure and functional properties of ulvan, a polysaccharide from green seaweeds. Biomacromolecules 2007, Vol. 8, 1765-1774.
[2] SignalP Server website page
[3] SIG-Pred: Signal Peptide Prediction website page
[4] Promega catalogue website page
[5] Qiagen catalogue website page
[6] santa cruz biotechnology, inc. catalogue website page
[7] WO 83/004261.
[8] ZoBell, CE 1941 Studies on marine bacteria. I. The cultural requirements of heterotrophic aerobes, J Mar Res 4, 41-75.
[9] Lahaye M., Bimalendu R., Baumberger S., Quernener B. and Axelos M., Procédéd'extraction des ulvanes [Method of extraction of ulvans], (1996) Hydrobiologia, 326/327, 473.
[10] LaemmLi UK and Favre M 1973 Links maturation of the head of bacteriophage T4.I. DNA packaging events. J Mol Biol 80:575-599.
[11] Bradford M M 1976; A rapid and sensitive method for the quantitation of microgram quantities of protein using the principle of protein-dye binding. Anal Biochem 72: 248-254.
[12] Gacesa P and Wusteman F S 1990 Plate assay for simultaneous detection of alginate lyases and determination of substrate specificity. Appl and Environ Microbiol 56: 2265-2267.
[13] Liu Y G and Whittier R F (1995), Thermal Asymmetric Interlaced PCR: Automatable Amplification and Sequencing of Insert End Fragments from P1 and YAC Clones for Chromosome walking. *Genomics* 25: 674-681.
[14] Liu Y G, Mitsukawa N, Oosumi T and Whittier R F (1995), Efficient isolation and mapping of *Arabidopsis thaliana* T-DNA insert junctions by thermal asymmetric interlaced PCR. *Plant J.* 8: 457-463.
[15] Cohen, S N, Chang A C Y, Hsu L (1972) Nonchromosomal antibiotic resistance in bacteria: genetic transformation of *Escherichia coli* by R-factor DNA. Proc. Natl. Acad. Sci. USA 69: 2110-2114.

The invention claimed is:

1. An ulvan lyase extracted from the microorganism deposited on 17 Jun. 2010 under number 1-4324 in the National Collection of Cultures of Microorganisms (CNCM) 25 rue du docteur Roux, 75724 Paris Cedex 15, France, having a molecular weight of 30-kD or 46-kD comprising the following four sequences in its peptide sequence:

PNDPNLK, (SEQ ID No. 9)

LLEVGNTGTFGSTGS, (SEQ ID No. 10)

DLANPDNV, (SEQ ID No. 11)
and

WNLPE. (SEQ ID No. 12)

2. The ulvan lyase according to claim 1, said protein being of SEQ ID No.1.

3. The ulvan lyase according to claim 2, further comprising SEQ ID No.2 at its C-terminal end.

4. The ulvan lyase according to claim 1, further comprising a signal sequence at its N-terminal end.

5. The ulvan lyase according to claim 4, wherein the signal sequence is SEQ ID No.3.

6. An isolated nucleic acid of SEQ ID No.5.

7. The nucleic acid according to claim 6, further comprising SEQ ID No.6 at its 3' end.

8. The nucleic acid according to claim 6, further comprising SEQ ID No.7 at its 5' end.

9. A vector comprising a nucleic acid, the nucleic acid chosen from SEQ ID No.5, SEQ ID No. 5 having SEQ ID No.6 at its 3' end, SEQ ID No. 5 having SEQ ID No.7 at its 5' end, and SEQ ID No. 5 having SEQ ID No.6 at its 3' end and SEQ ID No. 7 at its 5' end.

10. A host cell comprising a nucleic acid sequence or a vector, the nucleic acid chosen from SEQ ID No.5, SEQ ID No. 5 having SEQ ID No.6 at its 3' end, SEQ ID No. 5 having SEQ ID No.7 at its 5' end, and SEQ ID No. 5 having SEQ ID No.6 at its 3' end and SEQ ID No. 7 at its 5' end, and the vector comprising any of the foregoing nucleic acids.

11. A microorganism deposited on 17 Jun. 2010 under number 1-4324 in the National Collection of Cultures of Microorganisms (CNCM) 25 rue du docteur Roux, 75724 Paris Cedex 15, France.

12. A method of manufacturing an ulvan lyase, the method comprising:
 genetic recombination using a nucleic acid or a vector to produce the ulvan lyase, the nucleic acid chosen from SEQ ID No. 5, SEQ ID No. 5 with SEQ ID No.6 at its 3' end, SEQ ID No. 5 with SEQ ID No.7 at its 5' end, or SEQ ID No. 5 with SEQ ID No.6 at its 3' end and SEQ ID No.7 at its 5' end, and the vector comprising any of the foregoing nucleic acids;
 wherein the ulvan lyase having a molecular weight of 30-kD or 46-kD comprising at least one of the following four sequences in its peptide sequence:

PNDPNLK, (SEQ ID No. 9)

LLEVGNTGTFGSTGS, (SEQ ID No. 10)

DLANPDNV, (SEQ ID No. 11)
and

```
                                                (SEQ ID No. 12)
WNLPE.
```

13. A method of degrading ulvans comprising a step of bringing the ulvans into contact with an ulvan lyase, a host cell, or a microorganism in conditions permitting degradation of the ulvans by enzymatic digestion by said protein or said host or said microorganism;

wherein the ulvan lyase extracted from the microorganism deposited on 17 Jun. 2010 under number 1-4324 in the National Collection of Cultures of Microorganisms (CNCM) 25 rue du docteur Roux, 75724 Paris Cedex 15, France, having a molecular weight of 30-kD or 46-kD comprising the following four sequences in its peptide sequence:

```
                                                (SEQ ID No. 9)
PNDPNLK, (SEQ ID No. 10)
LLEVGNTGTFGSTGS, (SEQ ID No. 11)
DLANPDNV,
and (SEQ ID No. 12)
WNLPE;
and
``` wherein the host cell comprises a nucleic acid chosen from SEQ ID No. 5, SEQ ID No. 5 with SEQ ID No.6 at its 3' end, SEQ ID No. 5 with SEQ ID No.7 at its 5' end, or SEQ ID No. 5 with SEQ ID No.6 at its 3' end and SEQ ID No.7 at its 5' end; and wherein the microorganism is a culture of the microorganism deposited on 17 Jun. 2010 under number 1-4324 in the National Collection of Cultures of Microorganisms (CNCM) 25 rue du docteur Roux, 75724 Paris Cedex 15, France.

14. The ulvan lyase according to claim 2, further comprising a signal sequence at its N-terminal end.

15. The ulvan lyase according to claim 14, wherein the signal sequence is SEQ ID No.3.

16. The nucleic acid according to claim 7, further comprising SEQ ID No.7 at its 5' end.

\* \* \* \* \*